(12) United States Patent
Hobert

(10) Patent No.: US 7,125,976 B2
(45) Date of Patent: Oct. 24, 2006

(54) METHOD OF SCREENING FOR AGENTS INHIBITING CHLORIDE INTRACELLULAR CHANNELS

(75) Inventor: Oliver Hobert, New York, NY (US)

(73) Assignee: Trustees of Columbia University in the City of New York, New York, NY (US)

( * ) Notice: Subject to any disclaimer, the term of this patent is extended or adjusted under 35 U.S.C. 154(b) by 55 days.

(21) Appl. No.: 10/612,379

(22) Filed: Jul. 1, 2003

(65) Prior Publication Data

US 2005/0003363 A1    Jan. 6, 2005

(51) Int. Cl.
    *C07H 21/04* (2006.01)
    *C07H 21/02* (2006.01)
    *C12P 21/02* (2006.01)
    *C70K 14/435* (2006.01)

(52) U.S. Cl. .................. 536/23.5; 536/23.1; 435/69.1; 435/70.1; 530/350

(58) Field of Classification Search ............... 536/23.5; 435/320.1, 252.3, 325, 254.11, 69.1
See application file for complete search history.

(56) References Cited

U.S. PATENT DOCUMENTS 6,465,715 B1    10/2002    Zwaal et al.

FOREIGN PATENT DOCUMENTS

WO    WO 02/24872 A2    3/2002

OTHER PUBLICATIONS

Sulston, Accession No. AL 132876.4, Nov. 15, 1999.*
Hogan, P. et al., "Organogenesis: Molecular Mechanisms of Tubulogenesis." Nat. Rev. Genet. 3(7):513-23, 2000.
Lubarksky, M. et al., "Tube Morphogenesis: Making and Shaping Biological Tubules." Cell 112(1):19-28, 2003.
J. Folkman and C. Haudenschild, "Angiogenesis in Vitro." Nature 288(5791):5551-6, 1980.
G.E. Davis and C.W. Camarillo, An Alpha 2 Beta 1 Integrin-Dependent Pinocytic Mechanism Involving Intracellular Vacuole Formation and Coalescence Regulates Capillary Lumen and Tube Formation in Three-Dimentional Collagen Matrix. Exp. Cell Res. 224(1):39-51, 1996.
G.J. Beitel and M.A. Krasnow, "Genetic Control of Epithelial Tube Size in the Drosophila Tracheal System." Development 127(15):3271-82, 2000.
R.J. Metzger and M.A. Krasnow, "Genetic Control of Branching Morphogenesis." Science 284(5420):1635-9, 1999.
G. Manning and M.A. Krasnow, in the Development of Drosophila Melanogaster M. Bate and A. Martinez Arias, Eds., Cold Spring Harbor Laboratory Press Cold Spring Harbor, NY, vol. 1:609-685, 1993 (N/A).

F.K. Nelson, et al., "Fine Structure of the *Caenorhabditis elegans* Secretory-Excretory System." J. Ultrastruct. Res. 82(2):156-71, 1983.
F.K. Nelson and D.L. Riddle, "Functional Study of the *Caenorhabditis elegans* Secretory-Excretory System Using Lazer Microsurgery." J. Exp. Zool. 231(1):45-56, 1984.
M. Buechner, "Tubes and the Single *C. elegans* Excretory Cell." Trends Cell. Biol. 12(10):479-84, 2002.
J.R. Wolff and T. Bar, "Seamless Endothelia in Brain Capillaries During Development of the Rat's Cerebral Cortex." Brain Res. 41(1):17-24, 1972.
Hogan and Kolodziej, "Organogenesis: Molecular Mechanisms of Tubulogenesis." Nat. Rev. Genet. 3(7):513-23, 2002 (N/A).
M. Buechner, et al., "Cystic Canal Mutants in *Caenorhabditis elegans* are Defective in the Apical Membrane Domain of the Renal (Excretory)." Cell. Dev. Biol. 214:227-241, 1999.
Harrop, et al., "Crystal Structure of a Soluble Form of the Intracellular Chloride Ion Channel CLIC (NCC27) at 1,4-A Resolution." (N/A).
Ashley, et al., "Challenging Accepted Ion Channel Biology: p64 and the CLIC Family of Putative Intracellular Anion Channel Proteins." Mol. Membr. Biol. 20:1-11, 2003.
Landry, et al., "Purification and Reconstitution of Chloride Channels from Kidney and Trachea." Science 244:1469-72, 1989.
Li and Weinman, "Chloride Channels and Hepatocellular Function: Prospects for Molecular Identification." Annu. Rev. Physiol. 64:609-633, 2002.

(Continued)

*Primary Examiner*—David S. Romeo
*Assistant Examiner*—Daniel C. Garnett
(74) *Attorney, Agent, or Firm*—Bryan Cave LLP

(57) ABSTRACT

The present invention isolates and characterizes the exc-4 gene of *C. elegans*, and identifies exc-4 as an orthologue of the human CLIC family of chloride intracellular channels. Accordingly, a nucleic acid having the sequence of SEQ ID NO.: 1 is disclosed, as well as recombinant vectors and host cells comprising the nucleic acid sequence of SEQ ID NO.: 1. Further, a number of screening methods are disclosed to identify putative agents that inhibit vertebrate, and preferably human, CLICs using *C. elegans* and exc-4 inhibition as a loss-of-function model for CLIC activity. Also disclosed is a method of determining whether a specific member of the CLIC gene family is involved in tubulogenesis, where the rescue of a *C. elegans* exc-4 excretory cell phenotype via expression of a transgenic CLIC gene of interest indicates that the CLIC gene of interest is involved in tubulogenesis. Finally, a method is disclosed of identifying putative vertebrate, and preferably human, CLIC inhibitors using transgenic *C. elegans* exc-4 mutant embryos, where expression of the transgene yields a CLIC product that rescues the exc-4 mutant phenotype. Agents of interest resulting in a reversionary exc-4 mutant phenotype are putative agents that inhibit CLIC expression or function.

12 Claims, 14 Drawing Sheets
(12 of 14 Drawing Sheet(s) Filed in Color)

OTHER PUBLICATIONS

Jentsch, et al., "Molecular Structure and Physiological Function of Chloride Channels." Physiol. Rev. 82(2):503-568, 2002.

Ronnov-Jessen, "Differential Expression of a Chloride Intracellular Channel Gene, CLIC4, in Transforming Growth Factor-Beta1-Mediated Conversion of Fibroblasts to Myofibroblasts." Am. J. Pathol. 161:471-480, 2002.

Tamir, et al., "Secretogogue-induced Gating of Chloride Channels in the Secretory Vesicles of Parafollicular Cells." Endocrinology 135(5):2045-2057, 1994.

Schlesinger, et al., "Characterization of the Osteoclast Ruffled Border Chloride Channel and its Role in Bone Resorption." J. Biol. Chem. 272(30):18636-18643, 1997.

Valenzuela, et al., "The Nuclear Chloride Ion Channel NCC27 is Involved in Regulation of the Cell Cycle." J. Physiol. 529(3):541-552, 2000.

Fernandez-Salas, et al., "p53 and Tumor Necrosis Factor Alpha Regulate the Expression of a Mitochondrial Chloride Channel Protein." J. Biol. Chem. 274:36488-36497, 1999.

Fernandez-Salas, et al., "mtCLIC/CLIC4, an Organellular Chloride Channel Protein is Increased by DNA Damage and Participates in the Apoptotic Response to p53." Mol. Cell Biol. 22:3610-3620, 2002.

Matthew Buechner, David Hall and Edward Hedgecock, "Exc Mutations Affect Apical Cytoskeleton." (Early 1995 Intenational Worm Meeting, Abstract 320, 1995.) (N/A).

Suzuki, et al., "A Putative GDP-GTP Exchange Factor is Required for Development of the Excretory Cell in *Caenorhabditis elegans*." EMBO Rep. 2:530-535, 2001.

* cited by examiner

|  | cxc-4(+) Embryos | | | | cxc-4(+) Larvae | | | | |
| --- | --- | --- | --- | --- | --- | --- | --- | --- | --- |
| Stage | 400' | 480' | 500' | 550' | 0hr | 0hr | 2hr | 4hr | 4hr |
| ER | + | ++ | +++ | +++ | ++ | ++ | ++ | + | + |
| Golgi (GO) | + | ++ | ++ | ++ | +++ | +++ | + | + | + |
| Vacuole (TU) | - | ++ | ++ | - | - | - | - | - | - |
| Lumen (TU) | - | - | - | + | ++ | ++ | ++ | ++ | ++ |
| Canaliculi (CI) | - | - | - | +/- | ++ | ++ | +++ | ++ | ++ |
| ER,GO / TU,CI | NA | 5:1 | 4:1 | 4:1 | 1:1 | 1:1 | 1:2 | 1:3 | 1:4 |

SEQUENCE LISTING

```
<160> NUMBER OF SEQ ID NOS: 18

<210> SEQ ID NO 1
<211> LENGTH: 873
<212> TYPE: DNA
<213> ORGANISM: C. elegans
```

```
<400> SEQUENCE: 1
atggcagaag cttaccagat ccaatcaaac ggagatcccc aatcaaaacc tcttctcgag      60
ctctacgtaa aagcgtcagg aattgatgct cgccgcattg gagccgatct tttctgtcag     120
gaattctgga tggagttgta tgctctttat gagattggag ttgcacgagt cgaagtgaag     180
actgtcaacg tgaattctga agcatttaag aagaactttc tcggagcaca accaccgatt     240
atgattgaag aggaaaaaga gctgacatac actgataatc gagagattga aggacggatc     300
tttcatttgg caaaggaatt caatgttcca ctctttgaaa aggatccatc cgctgagaag     360
agaatagaga acttgtacag gaacttcaaa ctgttcctgc gagcaaaagt agagttcgat     420
aagggaaaaa aggagccatc gagagttgaa gatcttccag cacagattaa agttcactac     480
aatcgagtct gtgagcaact atccaatatt gatcagttgc tatccgagag aaaatctcga     540
tatctacttg gaaacagtat gactgaatat gactgtgaac tgatgccacg tcttcatcat     600
attcgaatta ttggattgtc acttcttgga ttcgatattc cacataattt cactcatctc     660
tgggcttata tcctcactgc ataccgtaca gcagcattta ttgagagttg tcccgccgat     720
caggacatta ttcatcacta taagaacaa atgaatctgt tcacaaatca acgtgaaacc     780
ctccaatcgc caacaaaaac gcacacaatt ccggaaaaag tgctatcgga tattcgtgtt     840
aaaggacttg ctcccgatgt taatgttcat taa                                  873

<210> SEQ ID NO 2
<211> LENGTH: 241
<212> TYPE: PRT
<213> ORGANISM: Homo sapiens

<400> SEQUENCE: 2

Met Ala Glu Glu Gln Pro Gln Val Glu Leu Phe Val Lys Ala Gly Ser
1               5                   10                  15

Asp Gly Ala Lys Ile Gly Asn Cys Pro Phe Ser Gln Arg Leu Phe Met
            20                  25                  30

Val Leu Trp Leu Lys Gly Val Thr Phe Asn Val Thr Thr Val Asp Thr
        35                  40                  45

Lys Arg Arg Thr Glu Thr Val Gln Lys Leu Cys Pro Gly Gly Gln Leu
    50                  55                  60

Pro Phe Leu Leu Tyr Gly Thr Glu Val His Thr Asp Thr Asn Lys Ile
65                  70                  75                  80

Glu Glu Phe Leu Glu Ala Val Leu Cys Pro Pro Arg Tyr Pro Lys Leu
                85                  90                  95

Ala Ala Leu Asn Pro Glu Ser Asn Thr Ala Gly Leu Asp Ile Phe Ala
            100                 105                 110

Lys Phe Ser Ala Tyr Ile Lys Asn Ser Asn Pro Ala Leu Asn Asp Asn
        115                 120                 125

Leu Glu Lys Gly Leu Leu Lys Ala Leu Lys Val Leu Asp Asn Tyr Leu
    130                 135                 140

Thr Ser Pro Leu Pro Glu Glu Val Asp Glu Thr Ser Ala Glu Asp Glu
145                 150                 155                 160

Gly Val Ser Gln Arg Lys Phe Leu Asp Gly Asn Glu Leu Thr Leu Ala
                165                 170                 175

Asp Cys Asn Leu Leu Pro Lys Leu His Ile Val Gln Val Val Cys Lys
            180                 185                 190

Lys Tyr Arg Gly Phe Thr Ile Pro Glu Ala Phe Arg Gly Val His Arg
        195                 200                 205
```

Tyr Leu Ser Asn Ala Tyr Ala Arg Glu Glu Phe Ala Ser Thr Cys Pro
210                 215                 220

Asp Asp Glu Glu Ile Glu Leu Ala Tyr Glu Gln Val Ala Lys Ala Leu
225                 230                 235                 240

Lys

<210> SEQ ID NO 3
<211> LENGTH: 247
<212> TYPE: PRT
<213> ORGANISM: Homo sapiens

<400> SEQUENCE: 3

Met Ser Gly Leu Arg Pro Gly Thr Gln Val Asp Pro Glu Ile Glu Leu
1               5                   10                  15

Phe Val Lys Ala Gly Ser Asp Gly Glu Ser Ile Gly Asn Cys Pro Phe
                20                  25                  30

Cys Gln Arg Leu Phe Met Ile Leu Trp Leu Lys Gly Val Lys Phe Asn
            35                  40                  45

Val Thr Val Asp Met Thr Arg Lys Pro Glu Glu Leu Lys Asp Leu
50                  55                  60

Ala Pro Gly Thr Asn Pro Pro Phe Leu Val Tyr Asn Lys Glu Leu Lys
65                  70                  75                  80

Thr Asp Phe Ile Lys Ile Glu Glu Phe Leu Glu Gln Thr Leu Ala Pro
                85                  90                  95

Pro Arg Tyr Pro His Leu Ser Pro Lys Tyr Lys Glu Ser Phe Asp Val
            100                 105                 110

Gly Cys Asn Leu Phe Ala Lys Phe Ser Ala Tyr Ile Lys Asn Thr Gln
        115                 120                 125

Lys Glu Ala Asn Lys Asn Phe Glu Lys Ser Leu Leu Lys Glu Phe Lys
130                 135                 140

Arg Leu Asp Asp Tyr Leu Asn Thr Pro Leu Leu Asp Glu Ile Asp Pro
145                 150                 155                 160

Asp Ser Ala Gly Glu Pro Pro Val Ser Arg Arg Leu Phe Leu Asp Gly
                165                 170                 175

Asp Gln Leu Thr Leu Ala Asp Cys Ser Leu Leu Pro Lys Leu Asn Ile
            180                 185                 190

Ile Lys Val Ala Ala Lys Lys Tyr Arg Asp Phe Asp Ile Pro Ala Glu
        195                 200                 205

Phe Ser Gly Val Trp Arg Tyr Leu His Asn Ala Tyr Ala Arg Glu Glu
    210                 215                 220

Phe Thr His Thr Cys Pro Glu Asp Lys Glu Ile Glu Asn Thr Tyr Ala
225                 230                 235                 240

Asn Val Ala Lys Gln Lys Ser
                245

<210> SEQ ID NO 4
<211> LENGTH: 231
<212> TYPE: PRT
<213> ORGANISM: Homo sapiens

<400> SEQUENCE: 4

Lys Leu Gln Phe Val Lys Ala Ser Glu Asp Gly Glu Ser Val Gly His
1               5                   10                  15

Cys Pro Ser Cys Gln Arg Leu Phe Met Val Leu Leu Leu Lys Gly Val
                20                  25                  30

Pro Phe Thr Leu Thr Thr Val Asp Thr Arg Arg Ser Pro Asp Val Leu

-continued

Lys Asp Phe Ala Pro Gly Ser Gln Leu Pro Ile Leu Leu Tyr Asp Ser
 50                  55                  60

Asp Ala Lys Thr Asp Thr Leu Gln Ile Glu Asp Phe Leu Glu Glu Thr
 65                  70                  75                  80

Leu Gly Pro Pro Asp Phe Pro Ser Leu Ala Pro Arg Tyr Arg Glu Ser
                 85                  90                  95

Asn Thr Ala Gly Asn Asp Val Phe His Lys Phe Ser Ala Phe Ile Lys
            100                 105                 110

Asn Pro Val Pro Ala Gln Asp Glu Ala Leu Tyr Gln Gln Leu Leu Arg
        115                 120                 125

Ala Leu Ala Arg Leu Asp Ser Tyr Leu Arg Ala Pro Leu Glu His Glu
130                 135                 140

Leu Ala Gly Glu Pro Gln Leu Arg Glu Ser Arg Arg Phe Leu Asp
145                 150                 155                 160

Gly Asp Arg Leu Thr Leu Ala Asp Cys Ser Leu Leu Pro Lys Leu His
                165                 170                 175

Ile Val Asp Thr Val Cys Ala His Phe Arg Gln Ala Pro Ile Pro Ala
            180                 185                 190

Glu Leu Arg Gly Val Arg Arg Tyr Leu Asp Ser Ala Met Gln Glu Lys
        195                 200                 205

Glu Phe Lys Tyr Thr Cys Pro His Ser Ala Glu Ile Leu Ala Ala Tyr
210                 215                 220

Arg Pro Ala Val His Pro Arg
225                 230

<210> SEQ ID NO 5
<211> LENGTH: 253
<212> TYPE: PRT
<213> ORGANISM: Homo sapiens

<400> SEQUENCE: 5

Met Ala Leu Ser Met Pro Leu Asn Gly Leu Lys Glu Glu Asp Lys Glu
 1               5                  10                  15

Pro Leu Ile Glu Leu Phe Val Lys Ala Gly Ser Asp Gly Glu Ser Ile
                20                  25                  30

Gly Asn Cys Pro Phe Ser Gln Arg Leu Phe Met Ile Leu Trp Leu Lys
            35                  40                  45

Gly Val Val Phe Ser Val Thr Thr Val Asp Leu Lys Arg Lys Pro Ala
 50                  55                  60

Asp Leu Gln Asn Leu Ala Pro Gly Thr His Pro Pro Phe Ile Thr Phe
 65                  70                  75                  80

Asn Ser Glu Val Lys Thr Asp Val Asn Lys Ile Glu Glu Phe Leu Glu
                 85                  90                  95

Glu Val Leu Cys Pro Pro Lys Tyr Leu Lys Leu Ser Pro Lys His Pro
            100                 105                 110

Glu Ser Asn Thr Ala Gly Met Asp Ile Phe Ala Lys Phe Ser Ala Tyr
        115                 120                 125

Ile Lys Asn Ser Arg Pro Glu Ala Asn Glu Ala Leu Glu Arg Gly Leu
130                 135                 140

Leu Lys Thr Leu Gln Lys Leu Asp Glu Tyr Leu Asn Ser Pro Leu Pro
145                 150                 155                 160

Asp Glu Ile Asp Glu Asn Ser Met Glu Asp Ile Lys Phe Ser Thr Arg
                165                 170                 175

```
Lys Phe Leu Asp Gly Asn Glu Met Thr Leu Ala Asp Cys Asn Leu Leu
            180                 185                 190

Pro Lys Leu His Ile Val Lys Val Ala Lys Lys Tyr Arg Asn Phe
        195                 200                 205

Asp Ile Pro Lys Glu Met Thr Gly Ile Trp Arg Tyr Leu Thr Asn Ala
    210                 215                 220

Tyr Ser Arg Asp Glu Phe Thr Asn Thr Cys Pro Ser Asp Lys Glu Val
225                 230                 235                 240

Glu Ile Ala Tyr Ser Asp Val Ala Lys Arg Leu Thr Lys
                245                 250

<210> SEQ ID NO 6
<211> LENGTH: 251
<212> TYPE: PRT
<213> ORGANISM: Homo sapiens

<400> SEQUENCE: 6

Met Thr Asp Ser Ala Thr Ala Asn Gly Asp Asp Ser Asp Pro Glu Ile
1               5                   10                  15

Glu Leu Phe Val Lys Ala Gly Ile Asp Gly Glu Ser Ile Gly Asn Cys
            20                  25                  30

Pro Phe Ser Gln Arg Leu Phe Met Ile Leu Trp Leu Lys Gly Val Val
        35                  40                  45

Phe Asn Val Thr Thr Val Asp Leu Lys Arg Lys Pro Ala Asp Leu His
    50                  55                  60

Asn Leu Ala Pro Gly Thr His Pro Pro Phe Leu Thr Phe Asn Gly Asp
65                  70                  75                  80

Val Lys Thr Asp Val Asn Lys Ile Glu Glu Phe Leu Glu Glu Thr Leu
                85                  90                  95

Thr Pro Glu Lys Tyr Pro Lys Leu Ala Ala Lys His Arg Glu Ser Asn
            100                 105                 110

Thr Ala Gly Ile Asp Ile Phe Ser Lys Phe Ser Ala Tyr Ile Lys Asn
        115                 120                 125

Thr Lys Gln Gln Asn Asn Ala Ala Leu Glu Arg Gly Leu Thr Lys Ala
    130                 135                 140

Leu Lys Lys Leu Asp Asp Tyr Leu Asn Thr Pro Leu Pro Glu Glu Ile
145                 150                 155                 160

Asp Ala Asn Thr Cys Gly Glu Asp Lys Gly Ser Arg Arg Lys Phe Leu
                165                 170                 175

Asp Gly Asp Glu Leu Thr Leu Ala Asp Cys Asn Leu Leu Pro Lys Leu
            180                 185                 190

His Val Val Lys Ile Val Ala Lys Lys Tyr Arg Asn Tyr Asp Ile Pro
        195                 200                 205

Ala Glu Met Thr Gly Leu Trp Arg Tyr Leu Lys Asn Ala Tyr Ala Arg
    210                 215                 220

Asp Glu Phe Thr Asn Thr Cys Ala Ala Asp Ser Glu Ile Glu Leu Ala
225                 230                 235                 240

Tyr Ala Asp Val Ala Lys Arg Leu Ser Arg Ser
                245                 250

<210> SEQ ID NO 7
<211> LENGTH: 290
<212> TYPE: PRT
<213> ORGANISM: C. elegans

<400> SEQUENCE: 7
```

```
Met Ala Glu Ala Tyr Gln Ile Gln Ser Asn Gly Asp Pro Gln Ser Lys
1               5                   10                  15

Pro Leu Leu Glu Leu Tyr Val Lys Ala Ser Gly Ile Asp Ala Arg Arg
                20                  25                  30

Ile Gly Ala Asp Leu Phe Cys Gln Glu Phe Trp Met Glu Leu Tyr Ala
            35                  40                  45

Leu Tyr Glu Ile Gly Val Ala Arg Val Glu Val Lys Thr Val Asn Val
    50                  55                  60

Asn Ser Glu Ala Phe Lys Lys Asn Phe Leu Gly Ala Gln Pro Pro Ile
65                  70                  75                  80

Met Ile Glu Glu Lys Glu Leu Thr Tyr Thr Asp Asn Arg Glu Ile
                85                  90                  95

Glu Gly Arg Ile Phe His Leu Ala Lys Glu Phe Asn Val Pro Leu Phe
                100                 105                 110

Glu Lys Asp Pro Ser Ala Glu Lys Arg Ile Glu Asn Leu Tyr Arg Asn
                115                 120                 125

Phe Lys Leu Phe Leu Arg Ala Lys Val Glu Phe Asp Lys Gly Lys Lys
    130                 135                 140

Glu Pro Ser Arg Val Glu Asp Leu Pro Ala Gln Ile Lys Val His Tyr
145                 150                 155                 160

Asn Arg Val Cys Glu Gln Leu Ser Asn Ile Asp Gln Leu Leu Ser Glu
                165                 170                 175

Arg Lys Ser Arg Tyr Leu Leu Gly Asn Ser Met Thr Glu Tyr Asp Cys
                180                 185                 190

Glu Leu Met Pro Arg Leu His His Ile Arg Ile Ile Gly Leu Ser Leu
        195                 200                 205

Leu Gly Phe Asp Ile Pro His Asn Phe Thr His Leu Trp Ala Tyr Ile
    210                 215                 220

Leu Thr Ala Tyr Arg Thr Ala Ala Phe Ile Glu Ser Cys Pro Ala Asp
225                 230                 235                 240

Gln Asp Ile Ile His His Tyr Lys Glu Gln Met Asn Leu Phe Thr Asn
                245                 250                 255

Gln Arg Glu Thr Leu Gln Ser Pro Thr Lys Thr His Thr Ile Pro Glu
                260                 265                 270

Lys Val Leu Ser Asp Ile Arg Val Lys Gly Leu Ala Pro Asp Val Asn
                275                 280                 285

Val His
    290

<210> SEQ ID NO 8
<211> LENGTH: 25
<212> TYPE: DNA
<213> ORGANISM: Artificial
<220> FEATURE:
<223> OTHER INFORMATION: Primer

<400> SEQUENCE: 8
cactcaggct tacagcactc ttgac                                          25

<210> SEQ ID NO 9
<211> LENGTH: 23
<212> TYPE: DNA
<213> ORGANISM: Artificial
<220> FEATURE:
<223> OTHER INFORMATION: Primer

<400> SEQUENCE: 9
```
ttcacacaat ttcggcaggt tag                                                 23

<210> SEQ ID NO 10
<211> LENGTH: 51
<212> TYPE: DNA
<213> ORGANISM: Artificial
<220> FEATURE:
<223> OTHER INFORMATION: Primer

<400> SEQUENCE: 10
agtcgacctg caggcatgca agctcatatc tggaattagc ggtggttgtt g                  51

<210> SEQ ID NO 11
<211> LENGTH: 45
<212> TYPE: DNA
<213> ORGANISM: Artificial
<220> FEATURE:
<223> OTHER INFORMATION: Primer

<400> SEQUENCE: 11
agtcgacctg caggcatgca agctatcggg agcaagtcct ttaac                         45

<210> SEQ ID NO 12
<211> LENGTH: 45
<212> TYPE: DNA
<213> ORGANISM: Artificial
<220> FEATURE:
<223> OTHER INFORMATION: Primer

<400> SEQUENCE: 12
agtcgacctg caggcatgca agctatcggg agcaagtcct ttaac                         45

<210> SEQ ID NO 13
<211> LENGTH: 51
<212> TYPE: DNA
<213> ORGANISM: Artificial
<220> FEATURE:
<223> OTHER INFORMATION: Primer

<400> SEQUENCE: 13
agtcgacctg caggcatgca agctaatatg atgaagacgt ggcatcagtt c                  51

<210> SEQ ID NO 14
<211> LENGTH: 48
<212> TYPE: DNA
<213> ORGANISM: Artificial
<220> FEATURE:
<223> OTHER INFORMATION: Primer

<400> SEQUENCE: 14
agtcgacctg caggcatgca agctagaatt cacgttgaca gtcttcac                      48

<210> SEQ ID NO 15
<211> LENGTH: 48
<212> TYPE: DNA
<213> ORGANISM: Artificial
<220> FEATURE:
<223> OTHER INFORMATION: Primer

<400> SEQUENCE: 15
agtcgacctg caggcatgca agcttgcaac tccaatctca taaagagc                      48

<210> SEQ ID NO 16
<211> LENGTH: 45
<212> TYPE: DNA
<213> ORGANISM: Artificial

```
<220> FEATURE:
<223> OTHER INFORMATION: Primer

<400> SEQUENCE: 16
agtcgacctg caggcatgca agctatcggg agcaagtcct ttaac          45

<210> SEQ ID NO 17
<211> LENGTH: 35
<212> TYPE: DNA
<213> ORGANISM: Artificial
<220> FEATURE:
<223> OTHER INFORMATION: Primer

<400> SEQUENCE: 17
cttggggtac cccatggcag aagcttacca gatcc                     35

<210> SEQ ID NO 18
<211> LENGTH: 36
<212> TYPE: DNA
<213> ORGANISM: Artificial
<220> FEATURE:
<223> OTHER INFORMATION: Primer

<400> SEQUENCE: 18
catgccatgg catgttaatg aacattaaca tcggga                    36
```

METHOD OF SCREENING FOR AGENTS INHIBITING CHLORIDE INTRACELLULAR CHANNELS

COPYRIGHT NOTICE

A portion of the disclosure of this patent document contains material subject to copyright protection. The copyright owner has no objection to the facsimile reproduction by anyone of the patent document or the patent disclosure, as it appears in the Patent and Trademark Office patent file or records, but otherwise reserves all copyright rights.

FIELD OF THE INVENTION

The field of the invention relates to an isolated nucleic acid for exc-4, wherein the nucleic acid encodes a *C. elegans* orthologue of the human CLIC chloride intracellular channel family, as well as to methods of using the modulation of exc-4, or of the EXC-4 protein, to identify putative agents that inhibit CLIC activity or expression.

BACKGROUND OF THE INVENTION

The morphogenesis of biological tubes is central to the development of a wide variety of metazoan structures, from the simplest Cnidarian body plans to the vertebrate respiratory, excretory, and circulatory systems. Although biological tubes form by such distinct processes as the hollowing of single cells and the folding of epithelial sheets, in each case an inner lumen is surrounded by a surface of apical character generated by the polarized movement or growth of vesicles or vacuoles (Hogan, P., et al., Organogenesis: molecular mechanisms of tubulogenesis. *Nat. Rev. Genet.* 3(7):513–23, 2002; and Lubarsky, M. et al., Tube morphogenesis: making and shaping biological tubes. *Cell* 112(1):19–28, 2003). A recent model proposes a de novo generation of an apically polarized surface by polarized vesicle targeting and fusion (Lubarsky, et al., supra, 2003). In this model, while developing multicellular tubes target small apical secretory vesicles to a specified region of the plasma membrane where they undergo exocytosis, developing unicellular tubes target to the center of the cell one or more large vacuoles that have originated via a pinocytotic process of invagination (Lubarsky, et al., supra, 2003; see also, J. Folkman and C. Haudenschild, Angiogenesis in vitro. *Nature* 288(5791):551–6, 1980, and G. E. Davis and C. W. Camarillo, An alpha 2 beta 1 integrin-dependent pinocytic mechanism involving intracellular vacuole formation and coalescence regulates capillary lumen and tube formation in three-dimensional collagen matrix. *Exp. Cell Res.* 224(1):39–51, 1996).

In general, all developing tubes must achieve the common goals of cell polarization and the establishment and maintenance of tubular architecture, including the precise regulation of tube diameter (G. J. Beitel and M. A. Krasnow, Genetic control of epithelial tube size in the *Drosophila* tracheal system. *Development* 127(15):3271–82, 2000). Along a single tubular network, distinct morphogenetic strategies may be used to create tubes of different gauges, and these mechanisms are often conserved across phyla. For example, the process of epithelial tube budding generates both the branches of the mammalian lung and the largest branches of the *Drosophila* tracheal system (R. J. Metzger and M. A. Krasnow, Genetic control of branching morphogenesis. *Science* 284(5420):1635–9, 1999). Similarly, the smallest branches of the *Drosophila* tracheal system are generated via the process of single cell hollowing (G. Manning and M. A. Krasnow, in *The Development of Drosophila melanogaster*, M. Bate and A. Martinez Arias, Eds., Cold Spring Harbor Laboratory Press, Cold Spring Harbor, N.Y., Vol. 1:609–685, 1993), which is also used to generate fine capillaries during mammalian angiogenesis (see, J. Folkman and C. Haudenschild, supra, 1980; G. E. Davis and C. W. Camarillo, supra, 1996). Thus, evolutionarily conserved mechanisms may be expected to function to form tubular structures, and general clues about the morphogenesis and homeostasis of biological tubes may be provided by studying simple tubular networks found in invertebrate model systems.

A simple model of tubular morphogenesis is provided by the *Caenorhabditis elegans* excretory cell, a single cell that forms the major tubular component of the four cell nematode excretory system (F. K. Nelson, et al., Fine structure of the *Caenorhabditis elegans* secretory-excretory system. *J. Ultrastruct. Res.* 82(2):156–71, 1983; F. K. Nelson and D. L. Riddle, Functional study of the *Caenorhabditis elegans* secretory-excretory system using laser microsurgery. *J. Exp. Zool.* 231(1):45–56, 1984; and M. Buechner, Tubes and the single *C. elegans* excretory cell. *Trends Cell. Biol.* 12(10): 479–84, 2002). This cell extends branched tubular processes, termed canals, along the length of the body on the basolateral surface of the epidermis. These processes are seamless yet tunneled by an inner lumen that is closed at its four endings and is presumed to collect fluids and waste, which then empty into the excretory duct. Thus the excretory cell provides a highly tractable model of a seamless, unicellular, fine-gauge tube, such as are found in the secondary branches of *Drosophila* trachea (G. Manning and M. A. Krasnow, supra, 1993), vertebrate blood capillaries (particularly in the brain)(J. R. Wolff and T. Bar, 'seamless' endothelia in brain capillaries during development of the rat's cerebral cortex. *Brain Res.* 41(1):17–24, 1972), and in other vertebrate organs including the lung (Hogan and Kolodziej, Organogenesis: molecular mechanisms of tubulogenesis. *Nat. Rev. Genet.* 3(7):513–23, 2002; Lubarsky and Krasnow, supra, 2003).

The process of tubulogenesis has been partially elucidated by the identification of a number of excretory canal mutants (the so-called "exc mutants") that exhibit characteristic defects in the ability of the canals to form a tubule or regulate the diameter of the excretory cell lumen. (M. Buechner, Tubes and the single *C. elegans* excretory cell, *Trends Cell Biol.* 12(10):479–484, 2002; M. Buechner, et al., Cystic Canal Mutants in *Caenorhabditis elegans* are Defective in the Apical Membrane Domain of the Renal (Excretory) Cell. *Dev. Biol.* 214:227–241, 1999). All of the twelve exc mutants identified thus far (namely, exc-1, exc-2, exc-3, exc-4, exc-5, exc-6, exc-7, exc-8, exc-9, let-4, let-653, and sma-1) display cyst formation in the excretory canal of *C. elegans*, although each mutant presents a specific and distinguishing canal morphology, as well as a characteristic variation in cyst size, shape and position. (Buechner, et al., supra, *Dev. Biol.* 214:227–241, 1999). The exc-4 mutant genotype presents with severe regional enlargements of the excretory canal's interior lumen, marked further with partial septa, which often act to partially or completely occlude the excretory channel. (Buechner, et al., supra, *Dev. Biol.* 214: 227–241, 1999). Further, there is a variable thickness or even frequent absence of the channel cytoskeleton, together with an uneven distribution of the channel canaliculi (thin membranous collecting channels, closed at their distal ends, which feed into lumen of each excretory canal) and lumenal glycocalyx. (Buechner, et al., supra, *Dev. Biol.* 214:227–241, 1999).

Until the present invention, there has been no disclosure implicating a role in tubulogenesis for any member of the CLIC family of chloride intracellular channel proteins (hereinafter, "CLICs"). CLICs are small proteins that have the unusual property of translocating from a globular cystic form to an integral membrane form (Harrop, et al., Crystal structure of a soluble form of the intracellular chloride ion channel CLIC1 (NCC27) at 1.4-A resolution. *J. Biol. Chem.* 276:44993–5000, 2001), where the integral membrane form is associated with chloride channel activity (Ashley, et al., Challenging accepted ion channel biology: p64 and the CLIC family of putative intracellular anion channel proteins. *Mol. Membr. Biol.* 20:1–11, 2003; Landry, et al., Purification and Reconstitution of Chloride Channels from Kidney and Trachea. *Science* 244:1469–72, 1989; Li and Weinman, Chloride channels and hepatocellular function: prospects for molecular identification. *Annu. Rev. Physiol.* 64:609–633, 2002; and Jentsch, et al., *Physiol. Rev.* Molecular structure and physiological function of chloride channels. 82(2): 503–568, 2002). While work in cultured cell systems has indicated CLICs serve roles in a wide variety of diverse processes, such as cell motility (Ronnov-Jessen, Differential expression of a chloride intracellular channel gene, CLIC4, in transforming growth factor-beta1-mediated conversion of fibroblasts to myofibroblasts. *Am. J. Pathol.* 161:471–480, 2002), vesicle acidification (Tamir, et al., Secretogogue-induced gating of chloride channels in the secretory vesicles of parafollicular cells. *Endocrinology* 135(5):2045–2057, 1994), electroneutral acid secretion (Schlesinger, et al., Characterization of the osteoclast ruffled border chloride channel and its role in bone resorption. *J. Biol. Chem.* 272(30):18636–18643, 1997), cell cycle progression (Valenzuela, et al., The nuclear chloride ion channel NCC27 is involved in regulation of the cell cycle. *J. Physiol.* 529(3): 541–552, 2000) and apoptosis (Fernandez-Salas, et al., p53 and tumor necrosis factor alpha regulate the expression of a mitochondrial chloride channel protein. *J. Biol. Chem.* 274: 36488–36497, 1999; Fernandez-Salas, et al., mtCLIC/CLIC4, an organellular chloride channel protein, is increased by DNA damage and participates in the apoptotic response to p53. *Mol. Cell Biol.* 22:3610–3620, 2002), the exact in vivo function role of CLICs has been lacking due to the absence of animal models.

Matthew Buechner, David Hall and Edward Hedgecock first disclosed the existence and phenotype of the *C. elegans* exc-4 mutant in "Exc Mutations Affect Apical Cytoskeleton" (Early 1995 International Worm Meeting, Abstract 320, 1995) (hereinafter, "Buechner I"). In Buechner I, it is noted that electron microscopy and wheat germ agglutinin staining of mutants defective in excretory canal structure reveals four classes of defects at the apical surface of the excretory cell. One class of nematode mutants, comprising mutations in the exc-1, exc-2, exc-4, exc-5, exc-9, let-4 and let-653 gene loci, exhibit lumena that swell into large cysts coincident with the separation of the apical membrane from its cytoplasmic coat.

The exc-4 mutant phenotype was further characterized by Matthew Buechner, David Hall, Harshida Bhatt and Edward Hedgecock in "Cystic Canal Mutants in *Caenorhabditis elegans* Are Defective in the Apical Membrane Domain of the Renal Excretory Cell" (*Developmental Biology.* 214: 227–241, 1999) (hereinafter, "Buechner II"). In Buechner II, nematodes were mutagenized to yield 12 different excretory canal mutant phenotypes, wherein each phenotype was associated with mutation in one of the following excretory canal gene loci, to wit, the exc-1, exc-2, exc-3, exc-4, exc-5, exc-6, exc-7, exc-8, exc-9, let-4, let-653 and sma-1 gene loci. Further, three separate mutant alleles of exc-4 were identified, wherein the common phenotype was characterized by a widened lumen, a truncated excretory canal ending well short of the wild-type excretory canal phenotype, and a specific uniform cyst size, shape and position. Finally, using two factor and three factor tests, together with complementation studies, the exc-4 gene locus was roughly mapped as being between the eDf7 and unc54 markers on chromosome I.

Buechner I and Buechner II disclose the existence and characterization of an exc-4 mutant phenotype. Buechner II further identifies three separate mutant alleles of exc-4 (namely, rh133, n561, and n2400), and roughly maps the exc-4 locus to a position in between the unc-54 and eDf7 markers. However, neither of Buechner I or II disclose, suggest or enable a determination of the coding sequence for the exc-4 nucleic acid. Nor does either reference disclose any characterization of the EXC-4 protein. Further, Buechner I and II do not disclose, suggest or enable any method of using *C. elegans* as an animal model to examine the in vivo function of the CLIC family of chloride intracellular channel proteins. In fact, Buechner II teaches away from a determination that the exc-4 gene is a CLIC orthologue, since it speculates that all of the disclosed excretory canal genes code for functionally related proteins. However, until the present invention, none of the excretory canal genes had been identified as coding for a chloride intracellular channel protein. (See, by way of example, Jones and Baillie, Characterization of the let-653 gene in *C. elegans. Mol. Gen. Genet.* 248:719–726, 1995 (let-653 encodes a mucin); McKeown, et al., sma-1 encodes a $\beta_H$-spectrin homolog required for *C. elegans* morphogenesis. *Dev.* 125:2087–2098, 1998 (sma-1 encodes the $\beta_H$-spectrin protein); Fujita, et al., The role of the ELAV homologue EXC-7 in the development of the *Caenorhabditis elegans* excretory canals. *Dev Biol.* 256(2):290–301, 2003) (exc-7 encodes a nematode homologue to the neural RNA-binding protein ELAV); and Suzuki, et al., A putative GDP-GTP exchange factor is required for development of the excretory cell in *Caenorhabditis elegans*. EMBO Rep. 2:530–535, 2001) (exc-5 encodes a protein homologous to guanine nucleotide exchange factors)). Finally, neither reference discloses, suggests or enables any method of using screens modulating exc-4 expression (or EXC-4 function) to identify putative agents that inhibit CLIC expression, function or activity.

Various screening methods using *C. elegans* are identified by Zwaal, et al., in U.S. Pat. No. 6,465,715, entitled "Expression of DNA or proteins in *C. elegans*", issued on Oct. 15, 2002 (hereinafter "Zwaal"). Specifically, Zwaal discloses methods for identifying compounds that have an affect on the morphology of the excretory canal, wherein each method includes the expression of a transgene (either a reporter gene and/or a coding sequence for the tested compound) under the control of an excretory canal specific promoter. Using the method of Zwaal, the transgenic *C. elegans* is first contacted with a candidate compound suspected of being a modulator of the development of the excretory canal of *C. elegans*, where the transgenic *C. elegans* comprises any one of a disclosed number of excretory canal specific promoters operatively linked to a reporter gene. A transgenic *C. elegans* that exhibits an altered excretory phenotype as a result of exposure to the candidate compound is identified, and it is determined whether the compound is a modulator of the development of the excretory canal of *C. elegans*.

Zwaal does not disclose, however, the coding sequence of the exc-4 nucleic acid. Nor does Zwaal disclose any characterization of the EXC-4 protein. Further, Zwaal does not disclose, suggest or enable any method of using *C. elegans* as an animal model to examine the in vivo function of the CLIC family of chloride intracellular channel proteins. Finally, Zwaal does not disclose, suggest or enable any method of using screens modulating exc-4 expression (or EXC-4 function) to identify putative agents that inhibit CLIC expression, function or activity.

Accordingly, in light of the foregoing, there exists a need for an isolated nucleic acid encoding the exc-4 excretory canal gene of *C. elegans*. Further, a need exists for an animal model representing the in vivo function of the CLIC family of chloride intracellular channel proteins. Finally, there is a need for a high throughput, genetically tractable screen to identify putative agents that inhibit CLIC expression, function or activity.

SUMMARY OF THE INVENTION

The inventor has, for the first time, isolated and characterized the excretory canal gene exc-4 of the free-living nematode *C. elegans*. The discovery has important implications for elucidating the process of tubulogenesis, as exc-4 mutants present various developmental defects in the excretory cell of the excretory canal, including the presence of large, fluid-filled cysts and an inability to maintain a narrow lumen diameter. (M. Buechner, Tubes and the single *C. elegans* excretory cell. *Trends in Cell Biology* 12(10):479–484, 2002). In addition, the inventor has determined that the exc-4 gene encodes an orthologue to the human CLIC family of chloride intracellular channel proteins. This finding was highly unexpected, in that, until the disclosure of the present invention, chloride intracellular channel proteins have never been implicated in the development of the excretory canal of *C. elegans*, nor, indeed, in mediating tubulogenesis generally. Accordingly, as described in further detail below, the inventor discloses herein the first animal model for this family of ion channel proteins. Still further, the inventor has identified the CLIC chloride channel proteins as an attractive target for inhibiting tubulogenesis and/or angiogenesis in vertebrate systems, particularly in the formation of endothelial capillary cells in mammalian systems.

Accordingly, the invention provides herein an isolated nucleic acid having the sequence of SEQ ID NO.: 1, wherein the isolated nucleic acid encodes the *C. elegans* exc-4 gene. The invention still further provides a recombinant expression vector comprising the isolated nucleic acid of the present invention, as well as a host cell comprising the expression vector. Still further, the invention describes a method of generating an EXC-4 protein, comprising the steps of introducing the isolated exc-4 nucleic acid of the present invention into a suitable host cell, culturing the host cell under conditions whereby the exc-4 nucleic acid is expressed, and thereafter recovering the EXC-4 protein encoded by the exc-4 nucleic acid. Also provided is the isolated and purified EXC-4 protein, as well as an antibody directed to an EXC-4 protein.

A number of screening methods to identify inhibitors or antagonists of vertebrate, and preferably human, CLIC expression or function are also disclosed herein. Specifically, the present invention discloses a method of identifying a putative agent that inhibits CLIC expression or function, where the method comprises the first step of contacting a *C. elegans* embryo, or an isolated *C. elegans* embryonic excretory cell, with an agent of interest and observing the resulting phenotype. Where the resulting excretory cell phenotype of the developing *C. elegans* embryo (or isolated *C. elegans* excretory cell) is characteristic of an exc-4 *C. elegans* mutant, it can be determined that the agent of interest is a putative agent that inhibits CLIC expression or function. In another embodiment of the inventive method, a *C. elegans* embryo or isolated *C. elegans* embryonic excretory cell is contacted with an agent of interest, and the resulting levels of expression of the exc-4 allele are measured and compared to a suitable control. Where there is a reduced level of exc-4 expression relative to a suitable control, the agent of interest is a putative agent that inhibits CLIC expression. In yet another embodiment of the inventive method, a *C. elegans* embryo or isolated *C. elegans* embryonic excretory cell is contacted with an agent of interest, and the resulting levels of EXC-4 activity are measured and compared to a suitable control. Where there is a reduced level of EXC-4 activity relative to a suitable control, the agent of interest is a putative agent that inhibits CLIC expression.

Still further, the present invention discloses a method of determining whether a CLIC gene is involved in tubulogenesis, wherein the method comprises the following steps. First, a CLIC gene operatively linked to a *C. elegans* promoter is expressed in an embryonic exc-4 mutant of *C. elegans* or in an isolated embryonic excretory cell derived from an exc-4 mutant of *C. elegans*. Second, the resulting excretory cell phenotype is observed, wherein an excretory cell phenotype characteristic of wild-type exc-4 expression indicates that the CLIC gene is involved in tubulogenesis.

Finally, a method of identifying a putative agent that inhibits CLIC expression or function is disclosed, where the method uses an exc-4 mutant, or an isolated *C. elegans* embryonic excretory cell derived from an exc-4 mutant, that has been phenotypically rescued through the expression of a transgenic CLIC gene. The rescued transgenic exc-4 mutant, or isolated excretory cell derived from a rescued exc-4 mutant, is then contacted with an agent of interest. The observation of a reversionary excretory cell phenotype characteristic of an exc-4 *C. elegans* mutant indicates that the agent of interest is a putative agent that inhibits CLIC expression or function.

Additional aspects of the present invention will be apparent in view of the description that follows.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1 is a schematic depiction of the excretory system (F. K. Nelson, et al., supra, *J. Ultrastruct. Res.* 82:156–71,1983). Schematic drawings as well as schematic presentation of several neuroanatomical structures, including excretory cell, lateral seam cells and sheath cell anatomy, can be found at Wormatlas (www.wormatlas.org).

FIGS. 2A–2C show the cytoplasm of the excretory cell in adult animals, as visualized by the expression of gfp under the control of an excretory-cell specific promoter (bgIs312). FIG. 2A shows a wildtype strain, while FIGS. 2B and 2C show the exc-4 mutant phenotype. (see Examples 6 and 7).

FIG. 3 shows the apical surface of the lumen, visualized with an apically localized, non-functional EXC-4 (R202Stop)::GFP reporter construct. Wildtype is shown in top panel. (see Examples 6 and 7).

FIGS. 4–7 illustrate experimental data establishing that exc-4 codes for a CLIC-type chloride intracellular channel protein. FIG. 4 is a rendering of the map position of the exc-4 locus and schematic structure of constructs used for transformation rescue. Rescue was scored by assessing the existence of cysts. In the rescue with a 12.4 kb genomic fragment, three out of three transgenic exc-4(rh133) show almost 100% penetrant rescue (104/109 animals show no cysts; 29/31 control exc-4(rh133) animals show cysts). In the exc-4::gfp rescue experiment, 0/51 animals show excretory cell defects. (see Examples 6 and 7).

FIG. 5 shows the sequence of EXC-4 and its homology to CLIC human orthologs. Mutant alleles (rh133, n561 and n2400) are indicated. A prediction of EXC-4 secondary structure (upper dark and light bars, with dark indicating alpha-helices and light indicating beta-sheets) matches the secondary structure of crystallized human CLIC1 (lower dark and light bars). Numbers above the sequence indicate point of fusion to the GFP coding sequence, also shown in FIG. 7 and in FIG. 8B. The N-terminus of CLIC3 shown here differs from the previously published, human CLIC3 mRNA sequence (Z. Qian, et al., Molecular cloning and characterization of a mitogen-activated protein kinase-associated intracellular chloride channel. *J. Biol. Chem.* 274: 1621–7, 1999), which lacked a single nucleotide in its N-terminus, thus causing the correct N-terminus to be out of frame. The missing nucleotide was observed both in human genomic sequence as well as the mouse ortholog of CLIC3. The sequence of hCLIC1 is listed as SEQ ID NO.: 2; the sequence of hCLIC3 is listed as SEQ ID NO.: 4; the sequence of hCLIC4 is listed as SEQ ID NO.: 5; and the sequence of hCLIC5 is listed as SEQ ID NO.: 6. EXC-4 is listed as SEQ ID No.: 7. An additional human CLIC (hCLIC6, Genbank Accession No. Q96NY7) was identified by Strippoli, et al., in "Segmental paralogy in the human genome: a large-scale triplication on 1p, 6p, and 21q.", *Mamm. Genome* 13(8):456–62, 2002 (the disclosure of which, together with the associated hCLIC6 GenBank entry, is expressly incorporated by reference herein in its entirety). The hCLIC6 sequence has a high degree of homology to the previously discovered human CLICs.

FIG. 6 is a dendrogram of CLIC sequences from human (hCLIC1; hCLIC2; hCLIC3; hCLIC4; and hCLIC5), *Drosophila* (CG6776 and cG10997) and *C. elegans* (F13A7.10; F26H11.5 and EXC-4). GST Ω sequences (hGSTo1 and hGSTo2) were included as outliers due to their previously noted, distant similarity to CLIC channel protein (Dulhunty, et al., The glutathione transferase structural family includes a nuclear chloride channel and a ryanodine receptor calcium release channel modulator. *J Biol. Chem.* 276:3319–23, 2001). The GenBank Accession number for the exc-4 cDNA (listed at SEQ ID NO: 1) is AY308063.

FIG. 7 illustrates the tertiary structure of human CLIC 1 (S J. Harrop, et al., supra, *J. Biol. Chem.* 276:44993–5000, 2001). Points of fusion with GFP in the homologous EXC-4 sequence used to analyze EXC-4 localization are indicated. Small arrows indicate Nto C-terminal direction.

FIG. 8A depicts expression in an excretory cell. RFP tagged EXC-4 protein (center and right panel) localizes to the apical membrane of the canal lumen. In a transgenic GFP reporter strain, bgIs312, the cytoplasm of the excretory cell is labeled (left and right). The box in the right panel labels the region blown up in the left and middle panels. FIG. 8B depicts expression in seam cells. RFP tagged wild-type EXC-4 protein (center and right) localizes to the apical membrane of the seam cells; localization is directly adjacent to AJM-1::GFP (left and right). FIGS. 8C–8F depict expression in sensory neuron sheath cells. A transcriptional exc-4 GFP fusion ("exc-4prom fusion", all left panels) expresses in the phasmid sheath cells in the tail (8C, 8D) and the labial sheath cells in the head (8E, 8F). Phasmid and labial sensory dendrites are labeled with DiI (8C, 8E; middle panels). EXC-4::RFP localizes to the tip of the sheath cells (8D, 8F). FIGS. 8G–8H are schematic drawings of lateral seam cells shown in FIG. 8B and phasmid and labial sheath cells shown in FIGS. 8C–8F (see Wormatlas (www.wormatlas.org ) for schematic drawings as well as schematic presentation of several neuroanatomical structures described here, including excretory cell, lateral seam cells and sheath cell anatomy).

FIG. 9A illustrates GFP reporter fusion constructs (see Examples 5 and 6) used herein. Secondary structure elements are denoted within the exons in light gray (beta-sheets) and dark gray (alpha-helices). Previously proposed transmembrane alpha-helices are indicated in dark gray. Construct #1 shows GFP fused to wild-type EXC-4. Construct #2 shows GFP fused to EXC-4(P238L), the mutation corresponding to the n2400 allele. Construct #3 shows GFP fused at the position of the stop in the n561 allele (R202Stop). Construct #4 shows GFP fused after the PTM comprised by alpha-helix 1 plus beta-sheet 2. Construct #5 shows GFP fused after the truncated transmembrane element ('TTM') comprised by alpha-helix 1. Construct #6 shows exc-4 transcriptional GFP fusion. FIG. 9B shows GFP reporter fusion localization in transgenic animals. Fusions #1, #3, and #4 show intact translocation to the lumenal membrane, whereas fusions #2,#5, and #6 fail to translocate and remain in the cytoplasm. For correctly localized, mutant proteins (fusions #3 and #4), localization was assessed both in wild-type and in exc-4(rh133) mutant backgrounds in order to eliminate a potential contribution of wild-type channel proteins to the localization of the GFP construct. The bright spot opposite the nucleus observed in animals expressing fusion #3 was not consistently observed and its identity was not further pursued. ("n"=excretory cell nucleus; "l"=lumenal space).

FIGS. 10–13 illustrate a variety of experimental results elucidating the timing exc-4 function in *C. elegans*. FIG. 10 depicts wild-type and exc-4(rh133) mutant embryos showing the excretory cell labeled by the exc-4 transcriptional GFP reporter. The top panel is the wild-type embryo. The bottom panel is the exc-4 mutant embryo at comma plus 150 minutes, where the cystic phenotype is clearly visible (cysts are indicated with arrows).

FIG. 11 is a histogram illustrating the heat shock induced rescue of exc-4 cystic phenotype by exc-4 cDNA. The time of heat shock initiation (horizontal axis) is plotted against the percentage of animals showing rescue (vertical axis).

FIG. 12 is an inventory of membrane surface area. The surface area devoted to different forms of cytoplasmic organelles inside the maturing excretory canal cell was judged by eye from widely spaced serial thin section electron micrographs in staged embryos and young L1 larvae. (−) not present or very rare, (+) uncommon, (++) common, (+++) abundant.

FIG. 13 shows electron micrographs of serial sectioned embryos at different embryonic stages. The top row indicates the age of the embryo and the plane of the EM section. Electron micrographs of the excretory cell body (480, 500 minutes) and the excretory canal (550 min, Oh hatchee) are shown in the middle row. The bottom row depicts tracings from each EM image indicating excretory cell plasma membrane and lumenal membrane.

FIG. 14A is a view at low magnification showing the size of a cyst relative to the body diameter. Arrowheads indicate the cytoplasmic membrane of the excretory cell. FIG. 14B is a view at higher magnification showing the patchy circumferential distribution of canaliculi and electron dense apical cytoskeleton.

DETAILED DESCRIPTION OF THE INVENTION

Figure 1:
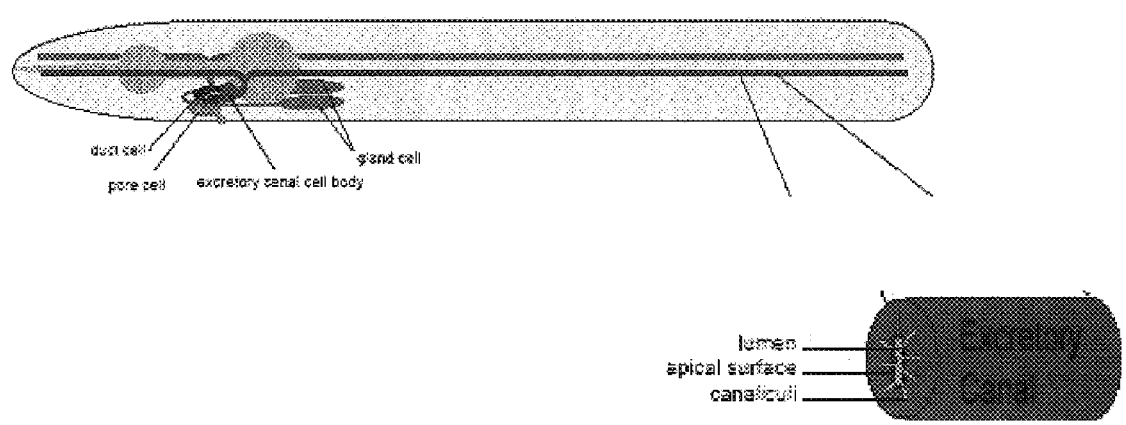
FIGS. 1–3 illustrate the excretory system of *C. elegans* and its disruption in exc-4 mutants.

The present invention is directed to the nucleic acid sequence of the wild-type C. elegans exc-4 gene, wherein the exc-4 gene encodes an intracellular chloride channel protein implicated in the development of the C. elegans excretory cell. The single cell excretory channel of C. elegans is a well-established model of tubulogenesis in higher organisms, i.e., in insects and vertebrates, and specifically is a model of endothelial capillary tube formation in mammalian systems. The present invention further discloses, for the first time, the homology of the nematode exc-4 gene to the human family of chloride intracellular channel proteins, or CLICs, and therefore provides the first animal model to study the in vivo activity of these CLICs. Still further, the discovery of this unexpected homology identifies the CLICs as a novel and attractive target to inhibit or downregulate the angiogenic process, especially the formation of endothelial capillary tubes. Accordingly, anti-CLIC agents may be candidate agents to limit vascularization in disease states associated with excessive angiogenesis (including, but not limited to, neoplasia and chronic inflammatory conditions, such as psoriasis).

Accordingly, the present invention provides an isolated nucleic acid having the sequence of SEQ ID NO.: 1, or alternatively, provides an isolated nucleic acid having the sequence complementary to SEQ ID NO.: 1, wherein the sequence of SEQ ID NO.: 1 encodes a nematode EXC-4 protein having intracellular chloride channel activity. As used herein, a "nucleic acid" may be genomic DNA, cDNA, RNA, or a peptide nucleic acid (PNA). Still further, the nucleic acid of the present invention may be single stranded or double stranded. By way of a non-limiting example, a double stranded RNA is provided herein, where one strand of the RNA molecule is complementary to all or a portion of the nucleic acid sequence of SEQ ID NO.: 1. Such a molecule would have utility in RNA interference applications, e.g., by blocking the expression of the exc-4 gene of C. elegans or the expression of a vertebrate CLIC orthologue (and preferably, by blocking the expression of a human CLIC orthologue, i.e., one or more of human CLIC 1, human CLIC 2, human CLIC 3, human CLIC 4, human CLIC 5 and human CLIC 6). A nucleic acid of the present invention is considered "isolated" where the nucleic acid is separated from other endogenous (i.e., non-recombinant) sequences that naturally flank the exc-4 gene in C. elegans and encode proteins other than the EXC-4 protein.

Also provided herein are mutated forms of these isolated nucleic acids, wherein the mutated nucleic acid may contain one or more deletions, insertions, missense, nonsense, point, polymorphism, rearrangement, or substitution mutations, or a combination thereof, and where the mutated forms of the nucleic acids encode for a mutant chloride intracellular channel protein. Specifically, the present invention discloses an isolated nucleic acid encoding a mutant EXC-4 protein, wherein the isolated nucleic acid has a sequence identical to the sequence of SEQ ID NO.: 1, except for the presence of one or more missense mutations, nonsense mutations, point mutations, substitutions, deletions, insertions, polymorphisms, or rearrangements. In a preferred embodiment, a mutated nucleic acid of the present invention has the sequence of one of the exc-4 mutant alleles rh133, n561 and n2400.

Preparation of the nucleic acid sequences disclosed herein will be obvious to one of ordinary skill in the art. For instance, the nucleic acid sequences may be generated using a DNA synthesizer, or, as exemplified herein, by PCR amplification. Further, the nucleic acid sequences of the present invention can be prepared from a natural source, or by using recombinant DNA techniques. In addition, the mutated nucleic acid sequences of the exc-4 gene can be made using standard mutagenesis techniques, including, but not limited to, chemical-induced, linker-induced, error-prone PCR induced, or radiation-induced random mutagenesis, or chemical, oligo-directed, or PCR-based site-directed mutagenesis.

Also provided for herein is an expression vector that comprises the isolated nucleic acid of the present invention. As used herein, the term "expression vector" refers to a vector or vehicle comprising a nucleic acid sequence coding for at least part of a gene product (i.e., wild-type or mutant EXC-4), wherein the nucleic acid sequence coding for the gene product is operably linked to and under the control of various regulatory sequences, such as promoters, attenuators, enhancers, polyadenylation signals, terminators, and the like, that provide for the expression of the coding sequence in a host cell. Any one of a wide number of expression vectors comprising the regulatory sequences necessary for the transcription and translation of wild-type or mutant exc-4 may be used, including, but not limited to, adenoviral vectors, adenoassociated vectors, herpes viral vectors, lentiviral vectors, phasmid vectors, plasmid vectors, retroviral vectors, or vaccinia viral vectors. In a preferred expression vector of the invention, the vector is a plasmid vector.

In a particular embodiment, the plasmid vector is the pcDNA3.1 vector (Invitrogen Life Technologies, Carlsbad, Calif.). However, other suitable expression vectors are well known in the art, and may include: pET-3d, pTriEx 1.1, pTriEx 2, pTriEx 3 and pTriEx 4 (all of Novagen, Madison, Wis.); pcDNA4, pcDNA6, pEXP1-DEST, pEXP2-DEST, pRSET, pET100, pET101, pET102, pET151, pET200, pFastBac, pMT/V5-His A, B and C, pMT/BiP/V5-His A, B and C, pMT-DEST48, pEF1, pEF4 and pEF6 (all of Invitrogen Life Technologies, Carlsbad, Calif.); and pTnT, pCI, pSP73, pSP72, pGEM, and pSI (all of Promega Corporation, Madison, Wis.). Still more vectors would be readily apparent to one of ordinary skill in the art, with any specific vector chosen according to the host system to carry the vector, levels of EXC-4 (or mutant EXC-4) expression desired, and the putative aim of EXC-4 (or mutant EXC-4) expression. A typical expression vector used in the present invention would comprise DNA elements that control initiation of transcription, such as a promoter, as well as DNA elements that control the processing of transcripts, such as a transcription termination/polyadenylation sequence. Suitable promoters would include strong constitutive promoters, including, but not limited to, the adenovirus major late promoter, the cytomegalovirus promoter, the promoter of the mouse metallothionein I gene, the mouse mammary tumor virus promoter, the Rous sarcoma virus promoter, the SV40 early promoter, or the TK promoter of Herpes virus. Alternatively, the promoter may be an inducible promoter, whereby the transcriptional initiation activity of the promoter can be modified by alteration of conditions external to the cell, usually by the addition of a non-toxic molecule or a change in physical culture conditions. Examples of suitable inducible promoters include, but are not limited to, an ecdysone-inducible promoter, a heat-shock regulated promoter, a metallothionein-regulated promoter, a steroid-regulated promoter, or a tetracycline-responsive promoter (e.g., a Tet-Off or Tet-On expression system, Clontech, BD Biosciences, Palo Alto, Calif.). Still further, the promoter may be a tissue-specific promoter that allows expression of the nucleic acid in a specific tissue or in a neoplasm derived from a specific tissue. Various tissue-specific promoters are enumerated in U.S. Pat. No. 6,277,621, entitled "Artificial chromosome constructs containing foreign nucleic acid sequences", the contents of which are expressly incorporated by reference herein. In one embodiment, the host cell is a nematode excretory cell and the promoter is an excretory cell specific promoter, such as, by way of non-limiting example, the bgls312 promoter (Devgen nv, Belgium), or any of the excretory cell specific promoters disclosed in U.S. Pat. No. 6,465,715, issued to Zwaal, et al., and entitled "Expression of DNA or proteins in C. elegans", the contents of which are expressly incorporated by reference herein.

Preferably, a vector of the present invention would further comprise a reporter gene, which allows for the preliminary evaluation of successful nucleic acid delivery into a cell or an organism. Common reporter genes used in the art encode for: secreted alkaline phosphatase; β-galactosidase; beta-glucoronidase; beta-lactamase; catechol dehydrogenase; chloramphenicol acetyltransferase; green fluorescent protein; horseradish peroxidase; luciferase; nopaline synthase; octapine synthase; and red fluorescent protein.

A host cell comprising a recombinant expression vector or nucleic acid of the present invention is also provided. The host cell may be prokaryotic, but is preferably eukaryotic. By way of example, the prokaryotic cell may be a bacterial cell such as *Agrobacterium tumefaciens, Bacillus subtilis, E. coli*, or any other suitable bacterium as would be obvious to one of ordinary skill in the art. Similarly, the eukaryotic cell may be cultured and derived from a wide variety of organisms, including chickens, hamsters, humans, insects, mice, nematodes or yeast. Some of the preferred host cells of the present invention include vertebrate endothelial cells, MDCK cells derived from the canine kidney, the excretory cell of *C. elegans*, terminal cells derived from the *Drosophila* tracheal system, human derived dermal microvascular endothelial cells (HDMEC), and telomerase immortalized human dermal microvascular endothelial cells (TIME).

The expression vector or nucleic acid of the present invention may be introduced into the desired host cell by any suitable means, including, where appropriate, viral-mediated transfection, or alternatively, such methods as calcium phosphate transfection, liposome-mediated transfection, microprojectile-mediated delivery, electroporation, biolistic transfection, or microinjection. In certain embodiments, an expression vector or nucleic acid of the present invention may be introduced into a host cell via an extracellular route of administration. For instance, the expression vector or nucleic acid may be introduced into the cells of a *C. elegans* nematode through the ingestion of food comprising the expression vector or nucleic acid, by immersing the nematode in a solution comprising the expression vector or nucleic acid, or by injecting the interstitial spaces or cavities of the worm with a solution comprising the expression vector or nucleic acid. Various delivery techniques into *C. elegans* are disclosed in Andrew Fire, et al., U.S. Pat. No. 6,505,559, entitled "Genetic Inhibition by Double-Stranded RNA", issued on Jan. 14, 2003, the contents of which are expressly incorporated by reference herein.

Also disclosed by the present invention are isolated EXC-4 proteins (mutant or wild-type) encoded from the nucleic acid of the present invention. In a preferred embodiment of the invention, the isolated EXC-4 protein has the wild-type amino acid sequence of SEQ ID NO.: 7. An EXC-4 protein of the present invention may be generated by any of the means commonly known in the art, including the synthesis of polypeptides in vitro, e.g., by chemical means or in vitro translation of mRNA, solid-phase peptide synthesis, solution-method peptide synthesis, and synthesis using any of the commercially-available peptide synthesizers. (see, e.g., *Modern Techniques of Peptide and Amino Acid Analysis* (New York: John Wiley & Sons, 1981; Bodansky, M., *Principles of Peptide Synthesis* (New York: Springer-Verlag New York, Inc., 1984). Further, an EXC-4 protein of the present invention may be generated from the expression in a host cell of the exc-4 nucleic acid disclosed herein, followed by isolation of the protein using any of the standard methods known in the art. As used herein, a protein is "isolated" when it is either free of chemical precursors or other chemicals (if generated by chemical means or by in vitro translation of mRNA) or substantially free of cellular matter, debris or unrelated protein (if generated from the expression of the exc-4 nucleic acid in a host cell).

Still further, antibodies or antibody fragments directed to the EXC-4 protein (wild-type or mutant) are disclosed. Methods of generating the antibodies or antibody fragments of the present invention are well known, and will be readily apparent to one of ordinary skill in the art. The antibodies of the composition may be single chain antibodies (see Ladner, et al., U.S. Pat. No. 4,946,778, entitled "Single polypeptide chain binding molecules"), monoclonal antibodies (see, E. Harlow and D. Lane, Eds., in "Antibodies—A Laboratory Manual", Cold Spring Harbor Laboratory, 1996), polyclonal antibodies (Harlow and Lane, supra, 1996), humanized antibodies (see Gregory Winter, U.S. Pat. No. 5,225,539, entitled "Recombinant altered antibodies and methods of making altered antibodies"), or chimeric antibodies (see Cabilly, et al., U.S. Pat. No. 4,816,567, entitled "Recombinant immunoglobin preparations"). Alternatively, they may be the antigen binding fragments of any of the foregoing, including, but not limited to, a Fab, $F(ab^1)_2$ or Fv fragment. These fragments may be generated by conventional recombination DNA techniques (Huse, W. D., et al., Generation of a large combinatorial library of the immunoglobulin repertoire in phage lambda. *Science*. 246:1275–1281, 1989) or by digestion of the antibody molecule with proteolytic enzymes, such as pepsin or papain.

Most commonly, antibodies are raised by the repeated immunization of a host animal, such as a donkey, horse, rat, mouse, goat, or preferably, a rabbit, with a suspension comprising the EXC-4 antigen. In a preferred method, the antigen is an artificial peptide comprising a short (i.e., 6 to 20) sequence of amino acid residues from the EXC-4 protein, where the artificial peptide is coupled to an immunogenic carrier molecule via a free sulfhydryl containing cysteine residue (or other suitable reactive group). Common immunogenic carrier molecules include bovine serum albumin, keyhole limpet hemocyanin, ovalbumin and PPd, a hapten protein derivative of tuberculin. Preferably, the non-specific immune response of the host animal is further strengthened by the simultaneous injection of an adjuvant, such as Freund's (complete and/or incomplete), mineral gel, an oil emulsion, dinitrophenol, or a lecithin derivative. Monoclonal antibodies, expressing a single antibody directed to a single epitope, are most commonly generated by the fusion of lymphoid cells from the spleen of the immunized animal with immortal myeloma cell lines. The resulting hybridomas can then be plated and selected for secretion of the desired antibody.

In a preferred embodiment of the invention, the antibody of the present invention is labeled with a detectable marker that would allow for the visualization or detection of complexes formed between the antibody and its associated EXC-4 target using standard immunoassay or imaging techniques. A large number of suitable detectable labels are well known in the art, including, but not limited to: enzymatic labels (alkaline phosphatase, alpha-glycerophosphate, aspariginase, beta-galactosidase, biotin/avidin/streptavidin complex, catalase, glucose-6-phosphate dehydrogenase, glucoamylase, glucose oxidase, horseradish peroxidase, malate dehydrogenase, ribonuclease, triose phosphate isomerase, urease, yeast alcohol dehydrogenase, etc.); fluorescent labels (allophycocyanin, fluorescein, fluorescein isothiocyanate, green fluorescent protein, o-phthaldehyde, phycocyanin, phycoerythrin, rhodamine, etc.); chemiluminescent labels (acridinium salt, imidazole, isoluminol, luminol, oxalate ester, theromatic acridinum ester, etc.); bioluminescent labels (aequorin, luciferin, luciferase, etc.); or radioactive labels (most commonly, $^3$H, $^{131}$I and $^{99}$Tc).

The present invention also discloses a number of methods of identifying putative agents that act to inhibit CLIC expression or function. As discussed in further detail below, agents identified as inhibitors of CLIC expression or function are prime candidate agents for the inhibition of CLIC-mediated tubulogenesis in vertebrate systems, particularly with regard to the development of single cell endothelial capillaries.

As used herein, an "agent" may include a peptide or polypeptide (including, but not limited to, natural peptides, synthetic peptides, analogs, mimetics, phosphopeptides, antagonists or dominant-inhibitory proteins), a nucleic acid (including, but not limited to, double or single stranded RNA or DNA, small nuclear RNAs, small nucleolar RNAs, micro-RNAs, small temporal RNAs, short hairpin RNAs, small interfering RNAs, peptide nucleic acids, nucleic acid analogs, or oligonucleotide mimetics), an antibody (including, but not limited to, a polyclonal antibody, monoclonal antibody, chimeric antibody, humanized antibody, single chain antibody, or antibody fragment, including an Fab fragment, or an F(ab$^1$)$_2$ fragment), a drug, a small molecule, or any compound comprising any of the foregoing. In one embodiment of the invention, expressly and without limitation as to further embodiments, the agent of interest is one of indanyloxyacetic acid-94, N-ethylmalemide, or glutathione.

A putative agent identified using the method of the present invention will "inhibit" CLIC function or activity if it acts to (i) downregulate or completely inhibit CLIC expression or the expression of a protein required for CLIC expression or attenuation, either at the transcriptional, translation or post-translational phase, (ii) prevent or reduce CLIC activity (i.e., chloride intracellular channel activity, such as, without being bound to theory, electric shunting to dissipate electrical potential generated by a V-ATPase proton pump) by completely occlusive, partially occlusive, or competitive binding with the CLIC intracellular channel itself or with a molecule that interacts with or attenuates the CLIC intracellular channel, or (iii) inhibit the translocation of the CLIC intracellular channel from its globular cystic form to its integral ion-conducting transmembrane form.

The present invention further discloses a method of identifying a putative agent that inhibits CLIC expression or function, wherein the method comprises the steps of (a) contacting a *C. elegans* embryo or isolated *C. elegans* embryonic excretory cell with an agent of interest, wherein the *C. elegans* embryo or isolated *C. elegans* embryonic excretory cell comprises a wild-type exc-4 allele; and (b) observing the resulting excretory cell phenotype of the developing *C. elegans* embryo or isolated *C. elegans* excretory cell, wherein an excretory cell phenotype characteristic of an exc-4 *C. elegans* mutant indicates that the agent of interest is a putative agent that inhibits CLIC expression or function.

As indicated, the stated method may use either *C. elegans* embryos, or embryonic excretory cells derived from *C. elegans* embryos. Data from experiments regarding the timing of exc-4 function indicate that exc-4 is required when the excretory canal initially develops (see Example 8, below). Accordingly, for the purposes of the present invention, a *C. elegans* "embryo" is at a developmental stage prior to or during early 3-fold stage, and an "embryonic excretory cell" is an excretory cell derived from an embryo prior to or during early 3-fold stage. Therefore, the agent of interest must be contacted with the embryo or embryonic excretory cell prior to or during early 3-fold stage.

The culture of nematodes, including *C. elegans*, is well understood and routine to those of ordinary experience in the art. Generally, *C. elegans* is plated on nematode growth medium (agar, NaCl, peptone, calcium chloride, magnesium sulfate, potassium phosphate and cholesterol) that has been seeded with bacteria, such as the uracil auxotroph *E. coli* OP50. Further, since the excretory cell undergoes tubulogenesis ex vivo (Buechner, et al., supra, *Dev. Biol.* 214: 227–241, 1999), cultures of isolated *C. elegans* excretory cells may also be used in method of the present invention. One method of generating embryonic excretory cell cultures is by the shearing of embryos harvested from gravid adults, followed by suspension of the resulting cells. Preferably, the embryos are from transgenic adults, wherein the embryos express a reporter gene under the control of an excretory cell specific promoter. The sheared cell suspension may then be separated and sorted by FACS or a similar method in order to specifically enrich a culture for excretory cells. The embryonic cell suspensions may then be placed onto treated glass coverslips or culture plates. Id. Wild-type cultured embryonic excretory cells develop a straight process (unlike the branched processes seen in vivo), with a lumen extending from (and opening at) the cell body and continuing to the end of the process. Growth and development of the embryonic cultures is rapid, as a nematode culture can be expected to develop from one cell embryos to mature nematodes in approximately 3 days (at room temperature), with embryogenesis occupying a mere 14–16 window within that time frame. Similarly, the excretory cells derived from wild-type embryonic nematodes develop a straight process within approximately 12–24 hours. As a result, nematodes and isolated nematode cells make useful tools for high-throughput drug screens, since a sizeable number of worms can be grown up, synchronized, and cycled quickly, allowing for the rapid and simultaneous identification of a large number of putative inhibitory agents. Further, the genetic make up of *C. elegans* is well characterized (see, e.g., the "Genome sequence of the nematode *C. elegans*: a platform for investigating biology" in *Science* 282(5396):2012–8, 1998) and its genetic tractability well documented, increasing the adaptability of a *C. elegans* drug screen.

According to the method of the present invention, an agent of interest is "contacted" with a *C. elegans* embryo or isolated *C. elegans* embryonic excretory cell, so that the resulting excretory cell phenotype of the developing *C. elegans* embryo or isolated *C. elegans* excretory cell can be observed. An agent of interest may be "contacted" with the embryo or embryonic excretory cell in any suitable manner allowing for interaction of the agent of interest with the exc-4 gene, with transcripts of the exc-4 gene and/or with the EXC-4 protein, or, alternatively, with any gene, gene transcript or protein that either affects transcription, translation or post-translation of the exc-4 gene, or interacts directly or indirectly with the EXC-4 protein, either in its cytosolic or transmembrane form. Accordingly, the agent may be "contacted" with the embryo or embryonic excretory cell by adding the agent of interest to the growth media of the embryos or to the suspension media of the isolated excretory cells, by bathing the embryos or isolated excretory cells in a solution comprising the agent of interest, by injecting the embryo or excretory cell with a solution comprising the agent of interest, or by expressing within the embryo or excretory cell with a nucleic acid encoding the agent of interest.

A resulting excretory cell phenotype characteristic of an exc-4 *C. elegans* mutant indicates that the agent of interest is a putative agent that inhibits CLIC expression or function. As used herein, an "excretory cell phenotype characteristic of an exc-4 *C. elegans* mutant" is defined as an excretory cell comprising a widened lumen, a truncated excretory canal ending well short of the wild-type excretory canal phenotype, and an altered apical surface characterized by a set of large, closely packed cystic enlargements. Conversely, an "excretory cell phenotype characteristic of wild-type exc-4 expression" is defined as an excretory cell comprising the features seen in a wild-type *C. elegans* nematode, as exemplified by the schematic of FIG. 1. Specifically, the excretory cell of the wild-type nematode exhibits branched, tubular processes, shaped in an "H" configuration, which extend along the length of the body on the basolateral surface of the epidermis. These processes are seamless, yet tunneled by a continuous inner lumen that is closed at its four endings.

In an alternate embodiment of the invention, a putative CLIC inhibitory agent is identified by measuring the levels of expression of the exc-4 allele following contact with the agent of interest, wherein a reduced level of exc-4 expression as compared to a suitable control (i.e., expression levels measured in a wild-type *C. elegans* nematode, or in an excretory cell derived from a wild-type *C. elegans* nematode, in each case untreated with the agent of interest) indicates that the agent of interest is a putative agent that inhibits CLIC expression. This method may prove advantageous where the excretory canal phenotype is intermediate between a wild-type *C. elegans* nematode and a *C. elegans* exc-4 mutant. Alternatively, this method may prove useful in distinguishing agents acting on exc-4 expression versus those acting on EXC-4 function or activity. Levels of exc-4 expression may be identified using any of a wide variety of methods known to those of ordinary skill in the art, including, but not limited to, Northern analysis, Western blotting, or immunological techniques directed against the EXC-4 protein.

Still further, the present invention discloses a method of determining whether a CLIC gene is involved in tubulogenesis, wherein the method comprises the steps of: (1) providing an embryonic exc-4 mutant of *C. elegans* or an isolated embryonic excretory cell derived from an exc-4 mutant of *C. elegans*; (2) expressing a CLIC gene in the embryonic exc-4 mutant of *C. elegans* or isolated embryonic excretory cell derived from an exc-4 mutant of *C. elegans*, wherein the CLIC gene is operatively linked to a *C. elegans* promoter; and (3) observing the resulting excretory cell phenotype of the developing embryonic exc-4 mutant of *C. elegans* or isolated embryonic excretory cell derived from an exc-4 mutant of *C. elegans*, wherein an excretory cell phenotype characteristic of wild-type exc-4 expression indicates that the CLIC gene is involved in tubulogenesis. Accordingly, according to the present method, an expressed CLIC gene that rescues the exc-4 mutant phenotype is identified as a CLIC gene involved in tubulogenesis. In a preferred embodiment of the method, the CLIC gene is a human CLIC gene, and even more preferably, is a gene encoding for one of human CLIC 1 (SEQ ID NO.: 2), human CLIC 2 (SEQ ID NO.: 3), human CLIC 3 (SEQ ID NO.: 4), human CLIC 4 (SEQ ID NO.: 5), human CLIC 5 (SEQ ID NO.: 6), or human CLIC 6.

Even further, a method of identifying a putative agent that inhibits CLIC expression or function is disclosed, the method comprising the steps of: (1) providing a *C. elegans* embryo or isolated *C. elegans* embryonic excretory cell, wherein the *C. elegans* embryo is an exc-4 mutant or the isolated *C. elegans* embryonic excretory cell is derived from an exc-4 mutant; (2) expressing a CLIC gene in the embryonic exc-4 mutant of *C. elegans* or isolated embryonic excretory cell derived from an exc-4 mutant of *C. elegans*, wherein the CLIC gene is operatively linked to a *C. elegans* promoter and expression of the CLIC gene rescues the exc-4 mutant phenotype; (3) contacting the embryonic exc-4 mutant of *C. elegans* expressing the CLIC gene or isolated embryonic excretory cell derived from an exc-4 mutant of *C. elegans* expressing the CLIC gene with an agent of interest; and (4) observing the resulting excretory cell phenotype of the developing embryonic exc-4 mutant of *C. elegans* or isolated embryonic excretory cell derived from an exc-4 mutant of *C. elegans*, wherein a reversionary excretory cell phenotype characteristic of an exc-4 *C. elegans* mutant indicates that indicates that the agent of interest is a putative agent that inhibits CLIC expression or function. In a preferred embodiment of the method, the CLIC gene is from a human, and even more preferably, is a gene encoding for one of human CLIC 1 (SEQ ID NO.: 2), human CLIC 2 (SEQ ID NO.: 3), human CLIC 3 (SEQ ID NO.: 4), human CLIC 4 (SEQ ID NO.: 5), human CLIC 5 (SEQ ID NO.: 6), or human CLIC 6.

In yet another embodiment, a method of identifying a putative agent that inhibits CLIC activity is disclosed, the method comprising the steps of: (i) contacting a *C. elegans* embryo or isolated *C. elegans* embryonic excretory cell with an agent of interest; (ii) measuring the resulting levels of EXC-4 activity; and (iii) comparing the measured levels of EXC-4 activity in the treated *C. elegans* embryos or isolated excretory cells to levels of EXC-4 activity in a suitable control (i.e., EXC-4 activity in a wild-type, untreated *C. elegans* embryo or isolated *C. elegans* embryonic excretory cell). Where there is a reduced level of EXC-4 activity in the treated embryo or culture relative to a suitable control, the agent of interest is a putative agent that inhibits CLIC activity. Levels of EXC-4 activity may be measured directly (e.g., by measuring chloride conductance)(see, e.g., Warton, et al., Recombinant CLIC1 (NCC27) Assembles in Lipid Bilayers via a ph-dependent Two-state Process to Form Chloride Ion Channels with Identical Characteristics to Those Observed in Chinese Hamster Ovary Cells Expressing CLIC 1. *J. Biol. Chem.* 277(29):26003–26011, 2002; Tulk, et al., CLIC 1 inserts from the aqueous phase into phospholipids membranes, where it functions as an anion channel. *Am. J. Cell. Physiol.* 282:C1103–C1112, 2002) or indirectly (e.g., by observing the extent to which the excretory cell forms normally—an intermediate phenotype indicates intermediate levels of EXC-4 activity).

In a preferred embodiment of the invention, the putative agent identified as an inhibitor of CLIC expression or function using any of the methods disclosed herein is a candidate agent for inhibiting tubulogenesis or angiogenesis in vertebrates, and preferably, inhibiting tubulogenesis or angiogensis in humans. As defined herein, "tubulogenesis" refers to the development of biological tubes, wherein an inner lumen is surrounded by a surface of apical character generated by the polarized movement or growth of vesicles or vacuoles. "Angiogenesis" refers to the growth of new blood vessels from preexisting vessels, and more specifically to the process comprising the focal degradation, invasion, migration, proliferation, organization and reattachment of capillary endothelial cells to form new blood vessels. (see Goldberg, et al., U.S. Pat. No. 6,498,144, entitled "Use of scatter factor to enhance angiogenesis", issued Dec. 24, 2002, the contents of which are expressly incorporated herein in their entirety).

Whether or not the CLIC inhibitor identified using the methods above is also a candidate inhibitor of tubulogenesis and/or angiogenesis may be determined by testing the CLIC inhibitor in a tubulogenesis and/or angiogenesis assay, a large number of which are well known in the art. By way of non-limiting example, the CLIC inhibitor may be contacted with a culture of human dermal microvascular endothelial cells (HDMEC) or telomerase immortalized human dermal microvascular endothelial cells (TIME), either of which can be stimulated under appropriate culture conditions to either proliferate on a fibronectin matrix or differentiate into tubules on a collagen matrix. (see, e.g., Venetsanakos, et al., Induction of tubulogenesis in telomerase-immortalized human microvascular endothelial cells by glioblastoma cells. *Exp. Cell Res.* 273:21–33, 2002). Other standard assays include animal models (Folkman, et al., Isolation of a tumor factor responsible or angiogenesis. *J. Exp. Med.* 133:275–288, 1971; Gimbrone, et al., Tumor growth and neovascularization: an experimental model using the rabbit cornea. *J. Natl. Cancer Inst.* 52:413–427, 1974), chick embryo assays (Klagsbrun, et al., Tumor angiogenesis activity in cells grown in tissue culture. *J. Cancer Res.* 36:110–114, 1976); in vitro assays (Folkman and Haudenschild, supra, *Nature* 288:551–556, 1980); murine angiogenesis assays, and rat cornea angiogenesis assays (Polverini et al., Induction of neovascularization in vivo and endothelial proliferation in vitro by tumor-associated macrophages. *Lab. Invest.* 51:635–642, 1984).

The present invention is described in the following Examples, which are set forth to aid in the understanding of the invention, and should not be construed to limit in any way the scope of the invention as defined in the claims that follow thereafter.

EXAMPLES

Example 1

Strains Used

The following strains were used as indicated. Bristol N2 wild-type; NJ469 exc-4(rh133)I; MT1191 exc-4(n561); MT6169 exc-4(n2400)I; CB30 sma-1(e30)V; SU93 jcIs1: Is[ajm-1::gfp; unc-29(+); rol-6(su1006)] (all from the *Caenorhabditis* Genetics Center, University of Minnesota, Minneapolis, Minn.); and UG756 bgIs312 (Devgen nv, Belgium).

Example 2

Examination of Exc-4 Morphology

In exc mutants (for "excretory canal abnormal") the tubular structure of the excretory cell lumen is disrupted by swellings termed 'cysts' that have been proposed to model tubulocystic kidney disease (M. Buechner, et al., supra, *Dev. Biol.* 214:227–241, 1999). The disruption of tubular morphology in exc-4 mutants has been previously described to be an enlargement of the tubule diameter of the canal's interior lumen marked with partial septa (Id.).

Figure 2:
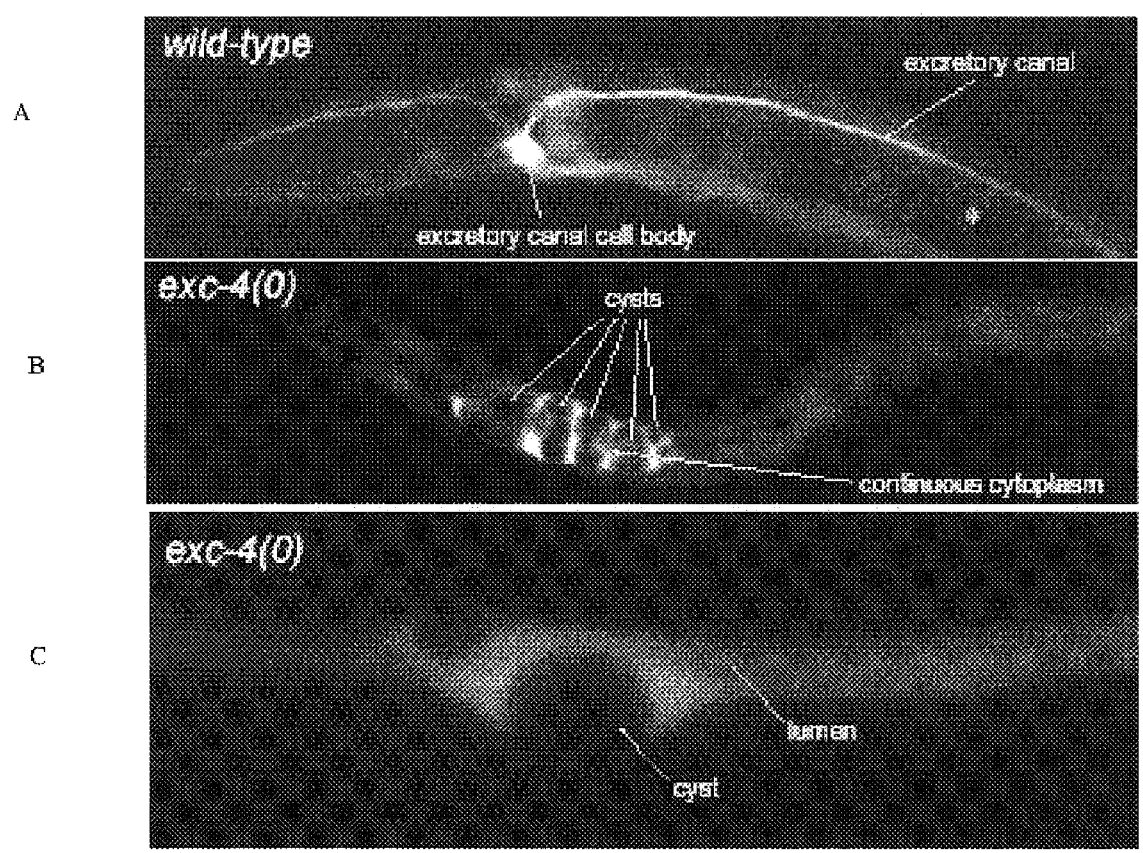
Figure 3:
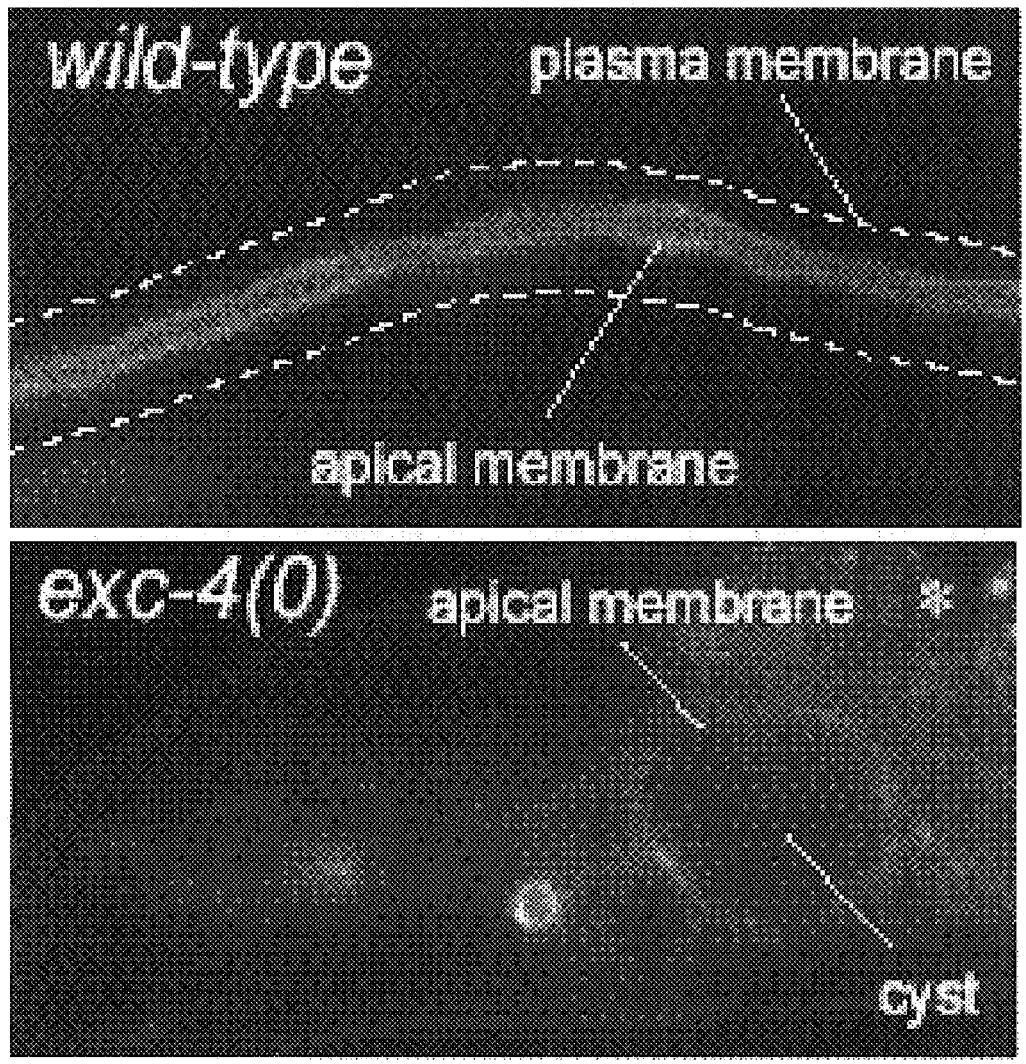
Figure 14:
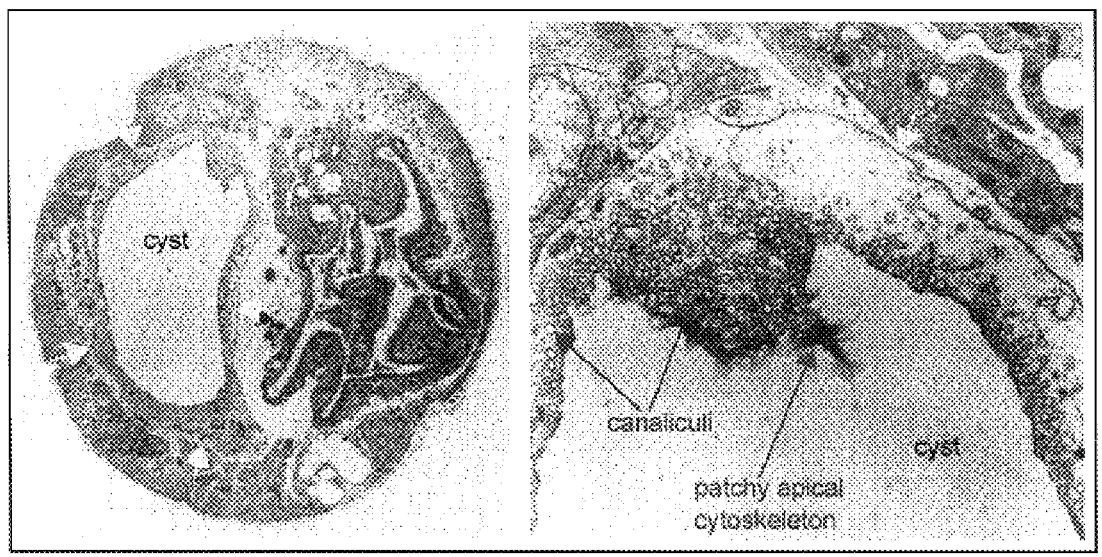
FIGS. 14A–14B depict electronic micrographs of serial sectioned exc-4(rh133) in the plain of an excretory canal cyst.

Using green fluorescent protein (gfp) markers that specifically label either the cytoplasm or the apical surface of the canal, a disruption of lumen structure in the exc-4 null allele rh133 was confirmed (FIGS. 1, 2 and 3). Specifically, in exc-4 mutant animals, the cytoplasmic marker narrowly labeled the septa between cysts and the apical marker labeled the entire perimeter of each cyst, establishing that septa are continuous with cytoplasm and that the entire cystic perimeter is apical in character (FIGS. 2 and 3). Moreover, in the small percentage of exc-4 mutant animals preserving largely intact canals, spherical cysts were visible in the cytoplasm beside the intact lumen (FIG. 3). Together these observations confirm that in exc-4 mutant animals, the topology of the apical surface is altered from a single, long, narrow tube to a set of large, closely packed cystic enlargements, some of which may be disconnected spheres (FIGS. 14A and 14B).

Whether the generation of these spheres and cysts depends on the presence of an intact apical cytoskeleton and may hence be explained by potential "pinching" forces exerted on the developing canal lumen was investigated. To this end, animals were used in which a component of the apical cytoskeleton, the beta-spectrin sma-1, is removed, resulting in a significant widening of the canal (M. Buechner, et al., supra, *Dev. Biol.* 214:227–241, 1999). If sma-1 is genetically eliminated in an exc-4 null mutant background, septated cysts are still observed, indicating that an intact apical cytoskeleton is not required for the exc-4 mutant phenotype to be manifested (data not shown).

Example 3

Mapping of exc-4 Locus and Homology Analysis

The exc-4 locus was mapped using SNP based mapping methods to a 130 kb interval on chromosome one containing seven predicted genes. SNP mapping was done using the Hawaiian *C. elegans* isolate CB4856. (see, Wicks, et al., Rapid Gene Mapping in *Caenorhabditis elegans* using a high density polymorphism map, *Nat. Gen.* 28:160–164, 2001; see also, Wicks and Plasterk, Snip-SNPs: a rapid and powerful mapping tool. *Worm Breeder's Gazette* 16(1): 28, 1999, and Wicks and Plasterk, snip-SNPs II: Mapping using bulked segregant analysis. *Worm Breeder's Gazette* 16(2): 24, 1999).

Generally, recombinant lines were obtained for each mutant exc-4 allele. Strains used were: NJ469 exc-4(rh133) I; MT1191 exc-4(n561)I; and MT6169 exc-4(n2400)I. Each mutant homozygous strain was mated with the highly polymorphic CB4856 isolate, and F1 cross-progeny were picked and individually plated. F2 homozygous mutant DNA was prepared for SNP analysis by lysing and releasing the genomic DNA of individual F2 homozygous mutants in worm lysis buffer (50 mM KCl; 10 mM Tris pH 8.3; 2.5 mM MgCl2; 0.45% NP-40 (IGEPAL); 0.45% Tween-20; 0.01% Gelatin), H2O and freshly added proteinase K. The polymorphic region of the F2 genomic DNA was amplified via polymerase chain reaction, and the polymorphism carried by each recombinant worm was determined using restriction digests.

Figure 4:
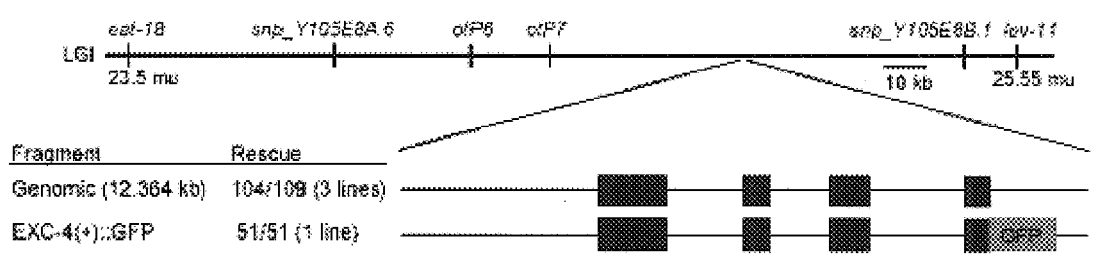
Figure 5:
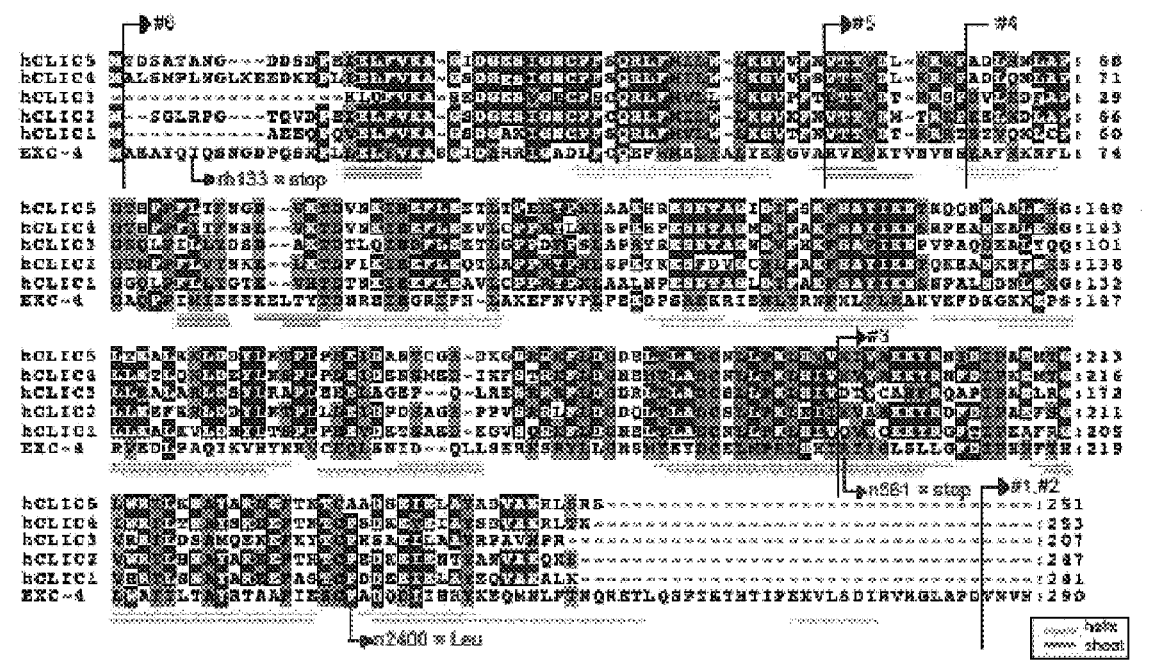

In the course of mapping, two new SNP markers, otP6 and otP7, were discovered. Predictions were done with Genefinder (available at www.softberry.com). A PCR product encompassing the coding region of a predicted intracellular ion channel protein fully rescued the mutant phenotype (FIG. 4). Molecular lesions in this channel protein are present in all three exc-4 mutant alleles, rh133, n561, and n2400 (FIG. 5), which appear indistinguishable in the severity of the excretory phenotype (94–100% of animals defective; n=30 to 32). The rh133 allele has an amber mutation in its sixth residue and therefore presumably eliminates all protein function.

Figure 6:
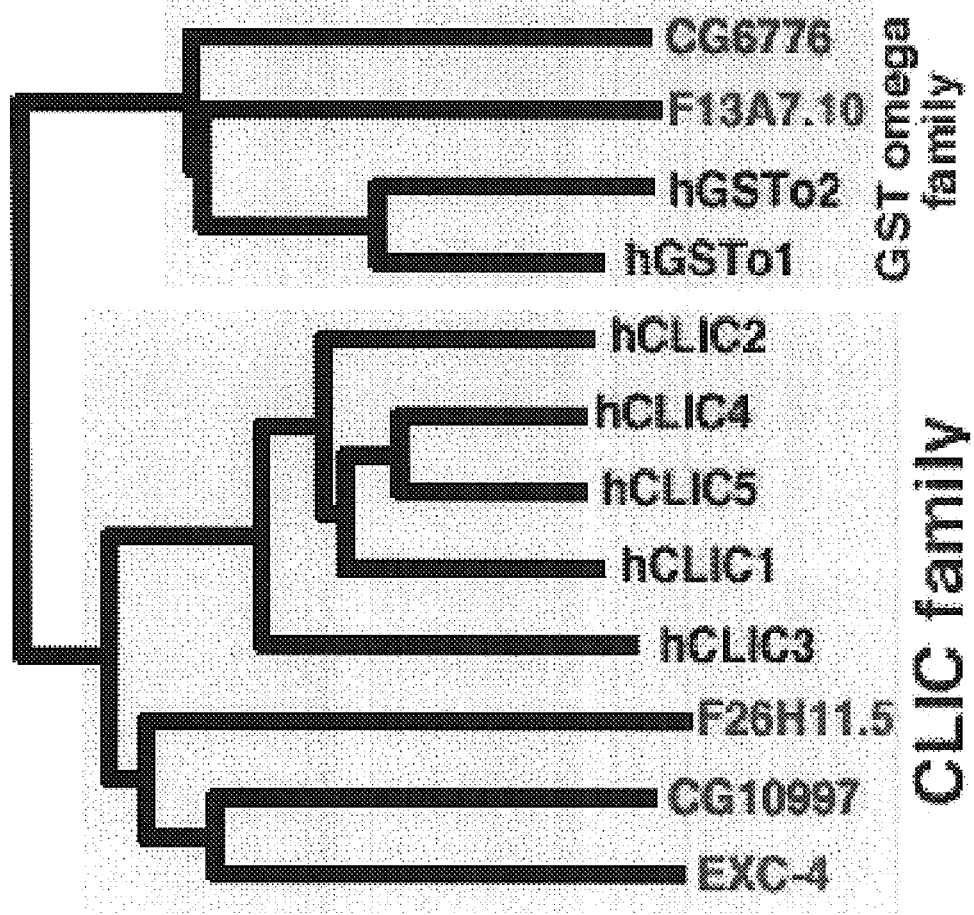

The ion channel protein encoded by the exc-4 locus is one of two C. elegans orthologs of the human CLIC ("chloride intracellular channel") family of chloride channel proteins (FIG. 6). The other C. elegans orthologue, F26H11.5, is mapped to chromosome II, and is of unknown function. Predicted cellular localization PSORT II analysis trained on yeast data indicates that the subcellular location of this protein is most likely in the cytoplasm or in the nucleus (GenBank Accession No. NP 497000).

Example 4

Expression Patterns and Subcellular Localization of Exc-4

The expression patterns and sublocalization of exc-4 were examined using gfp and red fluorescent protein (rfp; dsRed2) reporter genes generated by PCR fusion technology (O. Hobert, PCR fusion-based approach to create reporter gene constructs for expression analysis in transgenic C elegans. Biotechniques 32:728–30, 2002).

A. Expression Patterns

Transcriptional gfp fusion (in which 5 kb of upstream regulatory sequence was fused to gfp) and translational gfp and rfp fusion proteins (in which the same 5 kb of regulatory sequence plus all exons and introns of the exc-4 locus were fused to gfp or rfp) were generated. When expressed in transgenic animals, both transcriptional and translational fusion constructs show a similar tissue distribution. That the translational gfp reporter was fully functional for exc-4 activity and that it reveals the sites of endogenous gene expression was verified by testing its ability to rescue the exc-4 mutant phenotype, which it did (51 out of 51 transgenic animals show no excretory cell defects). Consistent with the presence of vertebrate CLIC orthologs in a variety of tissue types, exc-4 reporters are expressed in multiple tissue types, including the excretory cell (FIG. 8A), lateral hypodermis (FIG. 8B), tubular neuronal support cells in the head and tail (FIG. 8C-F), vulva, toroidal buccal hypodermal cells, pharyngeal muscle, rectal gland cell (data not shown), but not in body wall muscle, intestine or neurons.

B. Sublocalization of Exc-4

Figure 8:
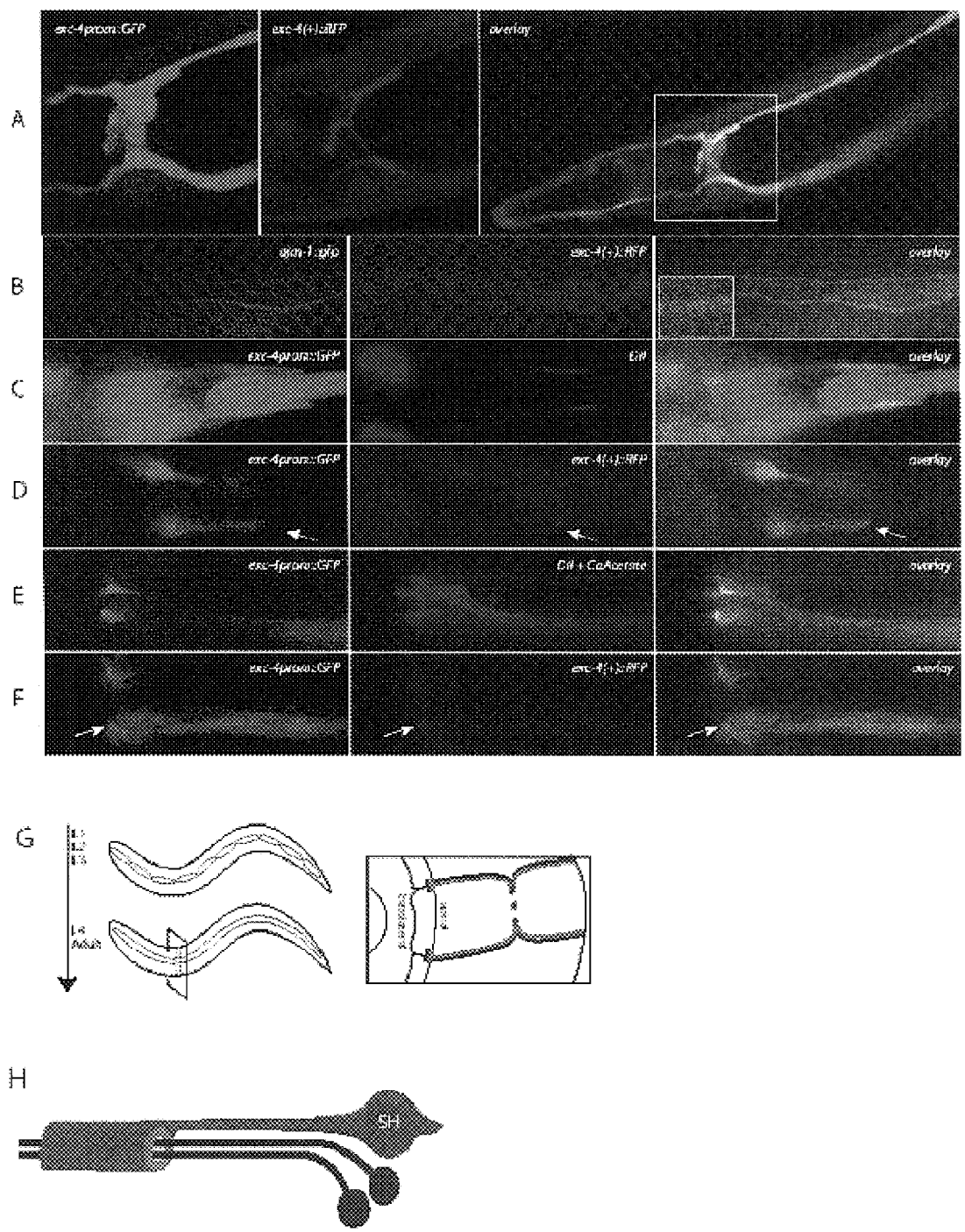
FIGS. 8A–8H depict the expression and localization of EXC-4 to membrane domains in different cell types.

Intriguingly, GFP and RFP-tagged EXC-4 protein showed striking patterns of subcellular localization. In the excretory cell, EXC-4::GFP localizes to the lumenal membrane (FIG. 8A). To verify this subcellular localization, a double reporter strain was created expressing a cytoplasmically localized gfp and the full coding sequence of exc-4 fused to RFP. Clear localization of RFP to the apical lumenal membrane was observed (FIG. 8A). In the hypodermis, EXC-4::RFP also shows highly specific membrane localization.

Specifically, in lateral seam cells, whose membranes extensively grow and eventually fuse to form an cylindrically-shaped syncytium along each lateral side of the animal, EXC-4::RFP localizes directly adjacent to the adherens junction marker AJM-1::GFP (W. A. Mohler, et al., Dynamics and ultrastructure of developmental cell fusions in the Caenorhabditis elegans hypodermis. Curr. Bio. 8:1087–90, 1998) to a compact subapical belt of plasma membrane termed the 'apical junction' (FIG. 8B). In phasmid and labial sheath cells, EXC-4::RFP specifically localizes to the extreme tip of the sheath cell membranes, where these glia-like cells fully encase neurons (FIG. 8D–F).

It is striking to note that EXC-4 localizes to very distinct membranes that undergo substantial membrane remodeling (growth and fusion) in order to create diverse tubular structures: Besides the excretory lumenal membrane, the tip of the sensory sheath cells enwrap the sensory ending, fuse with themselves after enwrapment and thus form an elongated, seamless tubular structure exposed to the sensory environment (Perkins, et al., Mutant sensory cilia in the nematode Caenorhabditis elegans. Dev. Biol. 117:456–87, 1986). Localization of EXC4::RFP again appears to be restricted to the apical lumen of the sheath channel.

Example 5

Testing Models of CLIC Membrane Insertion

To insert into the membrane, EXC-4 must, like other members of the CLIC family, be able change between its soluble and integral membrane conformations. Epitope tagging and digestion studies have indicated that the N-terminus is located on the extracytosolic side of membranes while the C-terminus is exposed to the cytoplasm (R. R. Duncan, et al., Cleavage site for sterol-regulated protease localized to a leu-Ser bond in the lumenal loop of sterol regulatory element-binding protein-2. J. Biol. Chem. 272:23880–6, 1997; R. Tonini et al., Functional characterization of the NCC27 nuclear protein in stable transfected CHO-K1 cells. Faseb J. 14:1171–8, 2000; and I. Proutski, et al., Overexpressed chloride intracellular channel protein CLIC4 (p64H 1) is an essential component of novel plasma membrane anion channels. Biochem. Biophys. Res. Commun. 297: 317–22, 2002).

Figure 7:
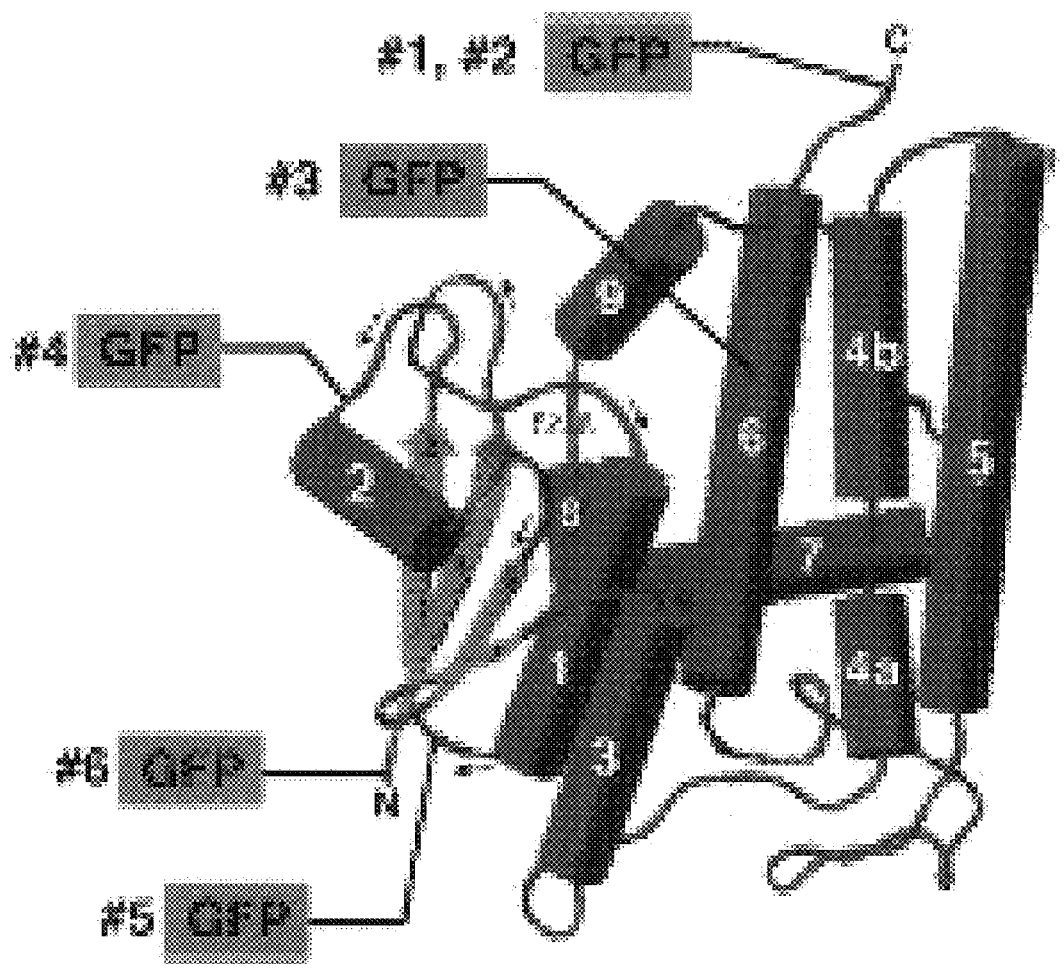

While the three dimensional structure of the soluble form of a human CLIC protein, CLIC-1, has been solved (FIG. 7) (J. Folkman and C. Haudenschild, supra, Nature 288:551–6, 1980), the transmembrane conformation of the protein is unclear, as is the nature and regulation of the conformational change between the two states. The structural elements observed in the globular form of the protein have led to the hypothesis that a hydrophobic domain located in the N-terminal domain of the globular structure serves as a single-pass transmembrane domain (Id.). Contrary to this hypothesis, it has been proposed that a C terminal multi-helix bundle, which shares several structural homologies to bacterial poreforming toxins, is inserted into the membrane, and, specifically, that the hydrophobic stretch comprising alpha-helix 6 functions as the leading helix in membrane insertion (B. A. Cromer, et al., From glutathione transferase to pore in a CLIC. Eur. Biophys. J. 31:356–64, 2002).

To test these competing models of CLIC membrane insertion, the lumenal membrane localization of EXC-4::GFP in the excretory cell was used to perform a structure-localization analysis. First, to verify the secondary structural homology between EXC-4 and human CLIC1, the inventor used secondary structure prediction algorithms on the EXC-4 sequence and found their consensus to almost precisely match the secondary sequence of the CLIC1 crystal structure (FIG. 4). Secondary structures were predicted using the PROF, PSIpred, APSSP2, Target99, and SSpro algorithms (available at: http://cubic.bioc.columbia.edu/predictprotein/submit_meta.html) and a consensus secondary structure was created using the most common prediction for each amino acid. In particular, both proposed transmembrane regions are predicted to adopt an alpha-helical structure. Thus EXC-4 presents a good model for CLIC membrane insertion.

Figure 9:
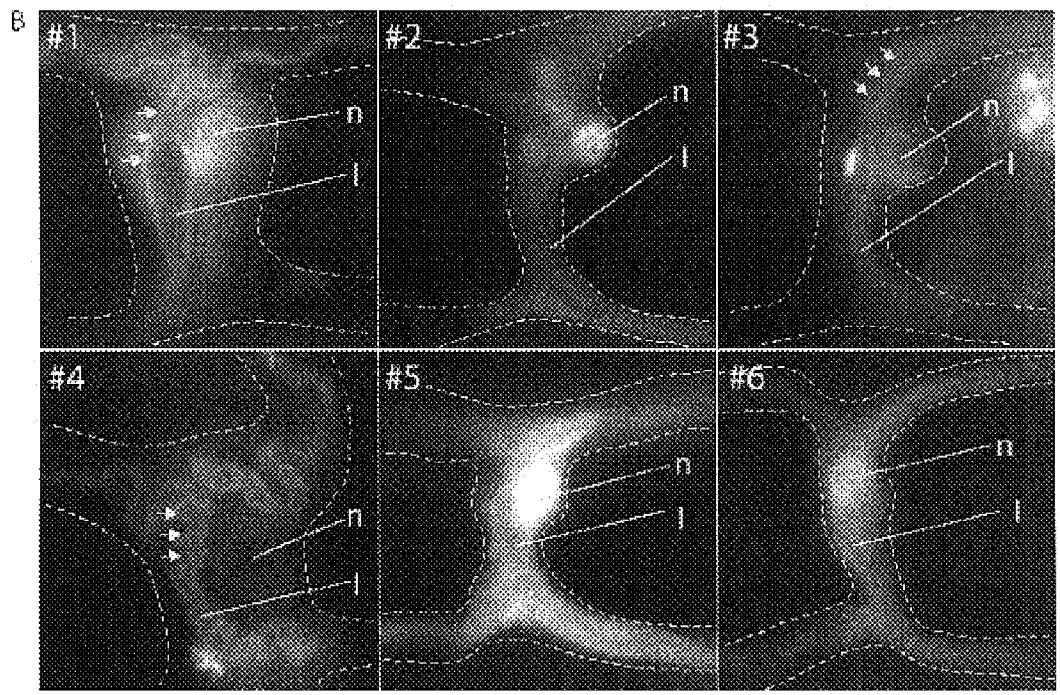
FIGS. 9A–9B show determinants of apical membrane localization of the EXC-4 protein.

Considering the proposed analogy between the C terminus of EXC-4 and pore-forming toxins, the molecular lesion found the exc-4 allele n561 is revealing since it introduces a premature stop (R202Stop) in the middle of the proposed transmembrane insertion alpha-helix 6 (B. A. Cromer, et al., supra, Eur. Biophys. J. 31:356–64, 2002). Secondary structure predictions of n561 predict only five remaining helical residues in alpha-helix 6, a span too short to cross the membrane. A translational gfp reporter was created mimicking the n561 allele by fusing gfp at the position of the premature stop. This reporter, while downregulated compared to the wild-type reporter, correctly localizes to the lumenal membrane, both in wild-type and exc-4 mutant backgrounds (FIG. 9B, #3). These results rule out alphahelix 6 and all downstream sequence as required for membrane localization, thereby excluding the proposed analogy to pore-forming toxins (B. A. Croner, et al., supra, Eur. Biophys. J. 31:356–64, 2002). In spite of its correct localization, the truncated protein is not functional since it does not rescue the exc-4(rh133) cystic phenotype and since a similar truncation present in the exc-4(n561) mutant strain shows lumenal defects that are as severe as observed in the molecular null allele rh133.

To test if the first proposed transmembrane region, close to the N-terminus of the protein (alpha-helix 1 plus betasheet 2), could mediate membrane insertion, a translational gfp reporter was created in which gfp was fused immediately after this region, encompassing 55 amino acids of the EXC-4 protein ("EXC-4(PTM)::GFP", for putative transmembrane helix). While also downregulated compared to the wild-type reporter, this construct was able to completely localize to the lumenal membrane, both in wild-type and exc-4 mutant backgrounds (FIG. 9B, #4).

Notably, otherwise wild-type animals carrying both EXC-4(PTM)::GFP and EXC-4(P238L)::GFP exhibited distinct types of abnormal, non-cystic excretory cellmorphology. In the case of EXC-4(PTM)::GFP, the excretory cell exhibits its usual elongated H-shaped structure and its lumen is topologically normal, however the normally straight canals exhibit tight corkscrew turns along their path (FIG. 9B #4). In the case of the non-localized n2400 reporter, the excretory cell exhibits its usual elongated H-shaped structure and its lumen is topologically normal, however the normally straight canals contain discrete serpentine regions exactly coextensive with brightly illuminated thread-like structures. The inventor notes that neither EXC-4(WT)::GFP nor EXC-4(R202Stop)::GFP cause such defects, which may reflect secondary neomorphic or antimorphic activities of otherwise highly downregulated alleles.

Deletion of beta-sheet 2 resulted in patchy membrane localization and a strong cytosolic partition that was not seen in EXC-4(PTM)::GFP (FIG. 4, #5). These data indicate that alpha-helix 1 plus beta-sheet 2 function as the key determinants for translocation of the protein from the cytosol into the membrane.

In the globular CLIC structure, a considerable conformation change must occur to allow membrane insertion given that alpha-helix 1 is shielded by alpha-helix 3 on one side and by alpha-helices 8 and 9 on the other (FIG. 7)(Harrop, et al., supra, J. Biol. Chem. 276:44993–5000, 2001). The molecular lesion of the exc-4 allele n2400 introduces a P238L missense mutation in a highly conserved proline between alpha-helices 8 and 9, which completely abrogates exc-4 function. It was noted that this proline may normally function as a helix breaking residue between the two helices. To determine the effect of this amino acid on CLIC localization, the P238L mutation was introduced in the correctly localized EXC-4::GFP construct and the localization of EXC-4(P238L)::GFP was examined in transgenic animals (see Example 7, below, for constructs used, and Example 8 for information on the generation of transgenic strains).

While downregulated compared to the wild-type translational reporter, EXC-4(P238L)::GFP failed to localize to the apical membrane, localizing instead to the cytoplasm (FIG. 9B, #2). Having shown above with the EXC-4(R202Stop):: GFP construct that the C-terminal half of the protein is itself dispensable for membrane insertion, the EXC-4(P238L) localization data suggests that the region of helices 8 and 9 participates in regulating the conformational change leading to insertion. For example, it could be envisioned that a reorientation of alpha-helices 8/9 is required for membrane insertion. Their absence would obliterate the need for reorientation and thus would have no effect on insertion, yet their incorrect conformation prevents the reorientation from occurring and hence prevents membrane insertion. Given that CLIC channels are likely to be multimeric (Warton, et al., Recombinant CLIC1 (NCC27) assembles in lipid bilayers via a pH-dependent two-state process to form chloride ion channels with identical characteristics to those observed in Chinese hamster ovary cells expressing CLIC1. J. Biol. Chem. 277:26003–11, 2002), it was determined whether the function-disrupting P238L mutation may have a poisonous effect on the assembly of wild-type channels by analyzing the mutant phenotype of heterozygous exc-4(n2400) animals which contain one copy of the mutant channel and one copy of the wild-type channel. Excretory lumen formation is completely normal in these animals thus excluding the poisonous effect of the EXC-4(P238L) protein.

Example 6

DNA Constructs

Constructs were generated by PCR fusion (Hobert, supra, Biotechniques 32, 728–730, 2002); the fusion was either to the polylinker of the gfp vector pPD95.75 (a gift from A. Fire) or to the rfp coding sequence from the dsRed2 vector (Clontech, Inc.). The template was N2 genomic DNA, except for the exc-4(P238L) construct, which was amplified from exc-4(n2400) DNA.

The upstream primers at the 5'end are: 5'-CACTCAG-GCTTACAGCACTCTTGAC (SEQ ID NO.: 8) and 5'-TTCACACAATTTCGGCAGGTTAG (SEQ ID NO.: 9) for the nested primer. The fusion primers at the 3' end are (length of PCR product indicated in parenthesis):exc-4prom::gfp: 5'-AGTCGACCTGCAGGCATGCAAGCT-CATATCTGGAATTAGCGGTGGTTGTTG (SEQ ID NO.: 10)(6821 bp); exc-4prom::exc-4::gfp: 5'-AGTCGACCTG-CAGGCATGCAAGCTATCGGGAGCAAGTCCTTTAAC (SEQ ID NO.: 11)(12,856 bp); exc-4prom::exc-4::DsRed2: 5'-AGTCGACCTGCAGGCATGCAAGC-TATCGGGAGCAAGTCCTTTAAC (SEQ ID NO.: 12)(12,670 bp); exc-4prom::exc-4(R202Stop)::gfp: 5'-AGTCGAC- CTGCAGGCATGCAAGCTAATATGATGAAGACGTGG CATCAGTTC (SEQ ID NO.: 13) (10,434 bp); exc-4prom:: exc-4(PTM)::gfp: 5'-AGTCGACCTGCAGGCATG-CAAGCTAGAATTCACGTTGACAGTCTTCAC (SEQ ID NO.: 14)(7016 bp); exc-4prom::exc-4(TTM)::gfp: 5'-AGTCGACCTGCAGGCATGCAAGCTTG-CAACTCCAATCTCATAAAGAGC (SE ID NO.: 15)(6983 bp); and exc-4prom::exc-4(P238L)::gfp: 5'-AGTCGACCT-GCAGGCATGCAAGCTATCGGGAG-CAAGTCCTTTAAC (SEQ ID NO.: 16)(12,856 bp).

The hsp16-2::exc-4 expression construct was generated by obtaining a full length exc-4 cDNA from a Stratagene cDNA library through PCR amplification (primer sequences: 5' CTTGGGGTACCCCATGGCAGAAGCT-TACCAGATCC 3' (SEQ ID NO.: 17) and 5' CATGCCATG-GCATG+TTAATGAACATTAACATCGGGAGC (SEQ ID NO.: 18)) and subcloning of the amplicon into the Nco1 site of the pPD49.78 vector.

Example 7

Transgenic Arrays

The transgenic arrays were constructed through DNA microinjection into the N2 (wild-type) background with the marker pRF4/rol-6(d) co-injected at a concentration of 100 ng/μl. Rescuing exc-4 genomic DNA and hsp16-2::exc-4 were injected at 20 ng/μl, gfp and rfp constructs were injected at 10–60 ng/μl depending on construct. To assess rescue, the array was crossed into an exc-4 mutant background. The transgenic arrays are as follows: otEx669, 670: Ex[exc-4prom::gfp]; otEx671–676: Ex[exc-4prom::exc-4:: gfp]; otEx718, 719: Ex[exc-4prom::exc-4::DsRed2]; otEx702–704: Ex[exc-4prom::exc-4(R202Stop)::gfp]; otEx789: Ex[exc-4prom::exc-4(PTM)gfp]; otEx814–816: Ex[exc-4prom::exc-4(TTM)::gfp]; otEx745–747: Ex[exc-4prom::exc-4(P238L)::gfp]; otEx810, 811: Ex[hsp16-2:: exc-4cDNA]; and otEx1000; 1001: Ex[hsp16-2::exc-4cDNA::gfp].

Example 8

Timing of exc-4 Function

Figure 10:
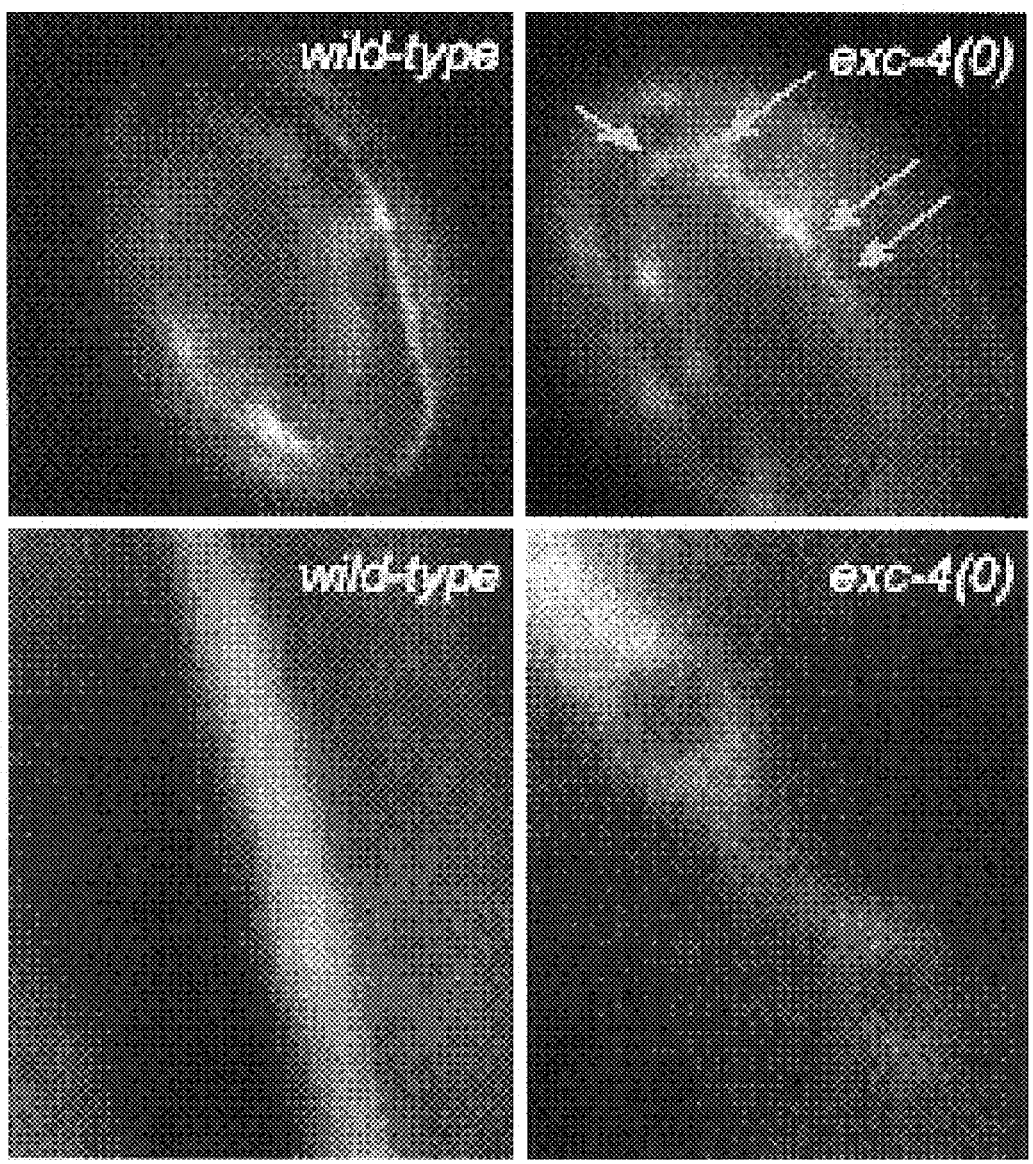

The localization of EXC-4 reporter constructs to the lumenal membrane and the aberrant morphology and topology of this membrane in exc-4 mutant animals indicated a role for EXC-4 in either the development or the stability of the apical surface. A developmental role was initially suggested by the fact that the exc phenotype first appears in late embryogenesis at the time of tubulogenesis (Buechner, et al., supra, Dev. Biol. 214:227–241, 1999). The inventor verified this using the gfp reporter labeling the excretory cell cytoplasm and found that in all exc-4(rh133) mutant embryos (n=26), cysts appear at multiple sites along the canal simultaneously with canal outgrowth (FIG. 10) . Further, while these embryonic cysts co-exist with developing tubules, indicating that tubulogenesis is not wholly impaired, the tubules that do form are not stable and disappear during the initial larval stages. These observations indicated that the requirement for exc-4 begins very early in lumen development.

To elucidate the timing of exc-4 function, attempts were made to rescue the exc phenotype at specific stages during development by using the heat inducible promoter from the ubiquitously expressed hsp16-2 gene to drive the complete exc-4 cDNA (D. Jones, et al., Structure, expression, and evolution of a heat shock gene locus in Caenorhabditis elegans that is flanked by repetitive elements. J. Biol. Chem. 261:12006–15, 1986). The independent hsp16-2::exc-4 transgenic lines were created as described above in Examples 6 and 7, and crossed into the exc-4(rh133) mutant background. Gravid adults were allowed to lay eggs for three hours and then heat shock was performed on the progeny at the appropriate stage. Embryos were heat shocked for 1 hour at 33 degrees Celsius, and L1 and L4 larvae were heat shocked for 2 hours at 33 degrees Celsius. Animals were scored for the presence of excretory cysts at each subsequent developmental stage. Embryonic heat shock was able to rescue the exc phenotype when performed before phenotypic onset (at pre-comma or comma stages), indicating perdurance of the EXC-4 protein. Indeed, a gfp tagged version, hsp16-2::exc-4::gfp, showed perdurance of gfp for several days (data not shown). It was also noted that fluorescence of the gfp tagged exc-4 is first visible 30 minutes after heat shock. The delay of 30 minutes is likely due to chromophore maturation.

Figure 11:
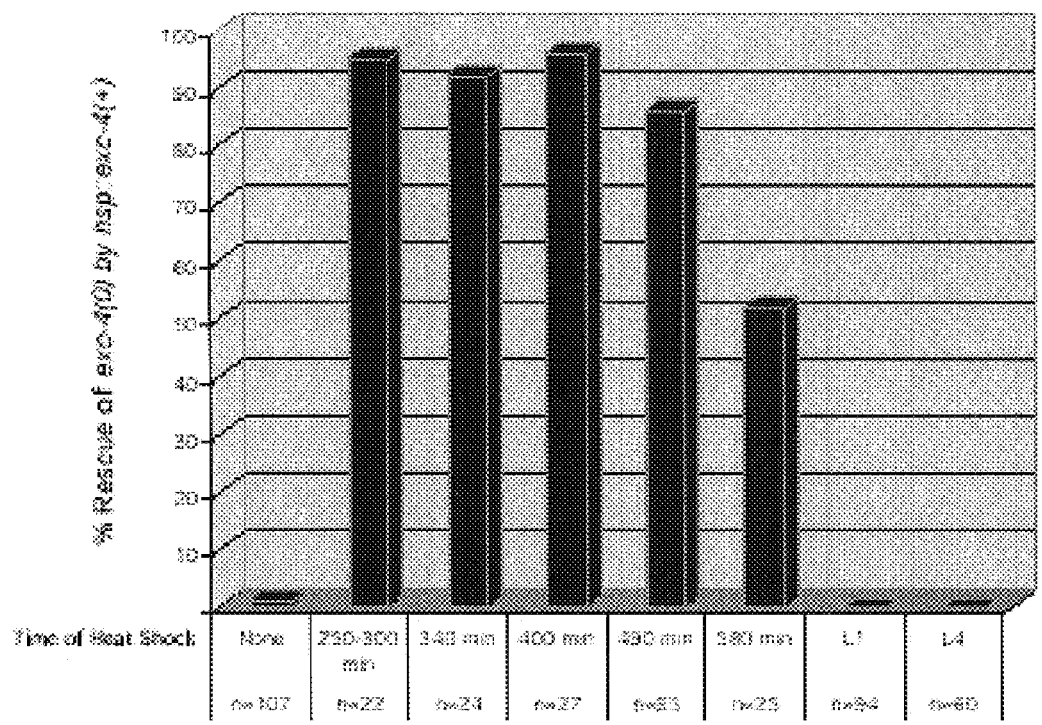

Induction of exc-4 expression during embryogenesis was able to fully rescue the exc phenotype in two independent transgenic lines (FIG. 11). In contrast, induction of exc-4 expression during the first larval stage or subsequent larval stages resulted in no rescue of the mutant phenotype (FIG. 11). These results demonstrate that the exc-4 is required during embryogenesis when the excretory canal initially develops and that an aberrantly formed tube can not be reverted to its wild-type morphology at later stages.

Figure 13:
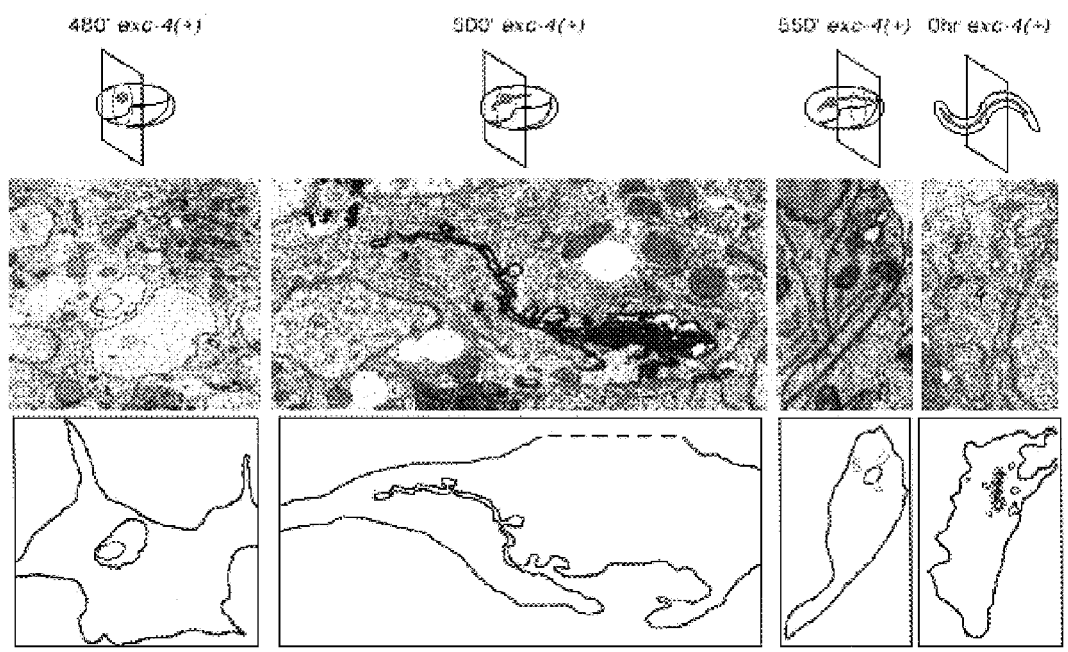

To define the role of exc-4 in tubulogenesis more precisely, attempts were made to rescue the exc phenotype by inducing hsp16-2::exc-4 during particular stages of lumen formation and outgrowth. To this end, the initial stages of excretory lumen formation in wild-type animals had to be characterized, which was done through the reconstruction of electron micrographs of serial sectioned wild-type embryos of different embryonic stages (FIGS. 12, 13)(Electron micrographs of serially sectioned embryos at different stages were collected using standard procedures by Richard Durbin and kindly provided to the Center for C. elegans Anatomy from MRC/LMB archives by J. Hodgkin). The excretory cell is born just after gastrulation and lacks all tubular characteristics through the 2-fold embryonic stage (FIG. 12). Shortly after the 2-fold stage, one or possibly two large vacuoles bearing striking characteristics of pinocytotic invaginations (dark membrane staining, inclusions, continuity with plasma membrane) appear within the excretory cell body (FIGS. 12,13).

It is intriguing to note that in vitro studies have revealed that intracellular tubes in endothelial capillary cells of vertebrates can also form via an initial pinocytotic vacuole formation step (Folkman and Haudenschild, Angiogenesis in vitro. Nature 288:551–6,1980; Davis and Camarillo, An alpha 2 beta 1 integrin-dependent pinocytic mechanism involving intracellular vacuole formation and coalescence regulates capillary lumen and tube formation in three-dimensional collagen matrix. Exp. Cell Res. 224:39–51, 1996).

Analysis of electron micrographs of later stage embryos demonstrates that, as previously described (Buechner, supra, Trends Cell Biol. 12(10): 479–484, 2002; Buechner, et al., supra, Dev. Biol. 214:227–241, 1999), during early 3-fold stage this vacuole sends tubular arms into the cytoplasmic projections of the developing H-shaped canal cell (FIG. 13). Finally, between mid 3-fold stage and hatching, the tubular arms of the vacuole undergo a collapse in diameter to assume a flattened, bi-lobed shape that is supported by newly apparent electron dense apical cytoskeletal material; simultaneously, many canaliculi develop around the main lumen (FIGS. 12, 13).

Having established this series of tubulogenetic events, the timing of exc-4 action was addressed. It was found that heatshock induction of exc-4 expression in an exc-4 mutant background before or during the time at which the developing vacuoles extend tubular arms is able to fully rescue the exc phenotype (FIG. 11). However, heat shock induced expression during or after the time of tubule flattening is not able to fully rescue the exc phenotype (FIG. 11).

The timing of exc-4 function indicates that exc-4 functions in early lumen formation rather than in late lumen remodeling. Consistent with this observation, electron micrographs of exc-4 reveal a that large number of canaliculi are successfully articulated around cysts, indicating that this process is unimpaired (FIG. 14) The existence of lumen, albeit of aberrant morphology and topology, in exc-4 mutants also indicates that the initial process of vacuole formation is not disrupted. Since EXC-4 function precedes the collapse of extended tubular arms to terminally differentiated, narrow lumens, it can be concluded that EXC-4 acts during the stage of extension of tubular arms from the initial vacuole(s).

Example 9

Conclusions

Several scenarios of how tube outgrowth occurs and how EXC-4 may be involved in this process as a putative chloride channel protein can be envisioned. It is likely that intracellular membrane growth, and hence outgrowth of the tubular arms, is achieved through the directed fusion of vesicles (Lubarsky and Krasnow, Tube morphogenesis: making and shaping biological tubes. *Cell* 112:19–28, 2003). Intracellular vesicle budding and fusion requires correct acidification of the fusing compartments, a process that requires V-ATPase proton pumps (Nishi and Forgac, The vacuolar (H+)-ATPases—nature's most versatile proton pumps. *Nat. Rev. Mol. Cell Biol.* 3:94–103, 2002). Several of those pumps, encoded by the vha genes, are indeed expressed in the excretory cell (Oka, et al., Three vha genes encode proteolipids of *Caenorhabditis elegans* vacuolar-type ATPase. Gene structures and preferential expression in an H-shaped excretory cell and rectal cells. *J. Biol. Chem.* 272:24387–92, 1997; Oka, et al., Four subunit a isoforms of *Caenorhabditis elegans* vacuolar H+-ATPase. Cell-specific expression during development. *J. Biol. Chem.* 276:33079–85, 2001; Oka, et al., Multiple genes for vacuolar-type ATPase proteolipids in *Caenorhabditis elegans*. A new gene, vha-3, has a distinct cell-specific distribution. *J. Biol. Chem.* 273:22570–6, 1998). Their appropriate function requires the existence of an electric shunt to dissipate the electrical potential generated by the proton pump, a function that has been previously proposed to be carried through by a CLIC associated channel (Landry, et al., supra, *Science* 244:1469–72, 1989; Landry, et al., Molecular cloning and characterization of p64, a chloride channel protein from kidney microsomes. *J. Biol. Chem.* 268:14948–55, 1993; and Redhead, et al., A ubiquitous 64-kDa protein is a component of a chloride channel of plasma and intracellular membranes. *Proc. Natl. Acad. Sci. USA* 89:3716–20, 1992) and which—in the context described here—may require EXC-4. In the absence of exc-4, intracellular vesicles destined to fuse with the growing tube may fail to do so, leading to the existence of the initially small cysts (as was observed in embryos) which grow by an EXC-4-independent mechanism during development to eventually adopt the large size observed in adults. Alternatively, as chloride channels have been shown to regulate water transport across membrane and cell swelling (Li and Weinman, Chloride channels and hepatocellular function: prospects for molecular identification. *Annu. Rev. Physiol.* 64:609–33, 2002), it could be envisioned that EXC-4 is required to precisely control the correct diameter of the growing tubule and/or the thinning of the vacuole which accompanies the outgrowth of the tubes from the vacuole. In the absence of exc-4, parts of the vacuole or the developing lumen may collapse and/or overswell, causing a rupture of the structure and thus producing cysts.

The role of EXC-4 in the tubular development of the *C. elegans* excretory lumen may reflect an evolutionarily conserved mechanism for shaping a vacuolar lumen into tubular form. While little is known about tubulogenesis in the seamless unicellular termini of the *Drosophila* tracheal system, the development of seamless capillaries from individual vertebrate endothelial cells, when observed in in vitro angiogenesis assays, occurs via a process strikingly similar to the development of the *C. elegans* excretory cell: large vacuoles arise via a pinocytotic process, enlarge, fuse, and then assume tubular morphology (Folkman and Haudenschild, supra, *Nature* 288:551–6,1980; Davis and Camarillo, supra, *Exp. Cell Res.* 224:39–51, 1996). If the vertebrate CLIC proteins function analogously to their invertebrate ortholog EXC-4 and are involved in the tube formation step during angiogenesis, these proteins may represent key targets for drugs aimed at disrupting the capillary network that supports tumor growth.

In summary, the present invention describes herein the first loss-of-function animal model for a CLIC family member. The subject study of exc-4 in the *C. elegans* excretory system demonstrates the in vivo requirement of this type of molecule and suggests a role for chloride conductance in the morphogenesis of biological tubes.

All publications, patent applications and issued patents cited in this specification are herein incorporated by reference as if each individual publication, patent application or issued patent were specifically and individually indicated to be incorporated by reference. Further, the earlier incorporation by reference of any specific publication, patent application or issued patent shall not negate this paragraph. The citation of any publication, patent application or issued patent is for its disclosure prior to the filing date of the subject application and should not be construed as an admission that the present invention is not entitled to antedate such disclosure by virtue of prior invention.

While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. An isolated nucleic acid having the sequence of SEQ ID NO.:1 or the sequence of a nucleic acid that encodes a polypeptide having the sequence of SEQ ID NO:7.

2. The nucleic acid of claim 1, wherein the nucleic acid is a DNA, RNA or a PNA.

3. The nucleic acid of claim 2, wherein the nucleic acid is single stranded or double stranded.

4. An isolated nucleic acid which encodes a mutant polypeptide selected from the group consisting of rh133, n561 and n2400.

5. A recombinant expression vector comprising the isolated nucleic acid of claim 1.

6. A recombinant expression vector comprising the isolated nucleic acid of claim 4.

7. A host cell comprising the recombinant vector of claim 5.

8. A host cell comprising the recombinant vector of claim 6.

9. A method of generating an EXC-4 protein, comprising the steps of:
   (a) introducing the nucleic acid of claim 1 into a host cell;
   (b) culturing the host cell under conditions allowing expression of the nucleic acid; and
   (c) recovering the EXC-4 protein.

10. A method of generating a mutant EXC-4 protein, comprising the steps of:
    (a) introducing the nucleic acid of claim 4 into a host cell;
    (b) culturing the host cell under conditions allowing expression of the nucleic acid; and
    (c) recovering the mutant EXC-4 protein.

11. The isolated nucleic acid sequence of claim 1 comprising the sequence of SEQ ID NO:1.

12. An isolated nucleic acid sequence that is fully complementary over the entire length to either SEQ ID NO:1 or to a polynucleotide sequence that encodes SEQ ID NO:7.

* * * * *